United States Patent [19]
Maiti et al.

[11] Patent Number: 5,994,521
[45] Date of Patent: Nov. 30, 1999

[54] FULL LENGTH TRANSCRIPT (FLT) PROMOTER FROM FIGWORT MOSAIC CAULIMOVIRUS (FMV) AND USE TO EXPRESS CHIMERIC GENES IN PLANT CELLS

[75] Inventors: Indu B. Maiti, Lexington, Ky.; Robert J. Shepherd, Portland, Oreg.

[73] Assignee: University of Kentucky Research Foundation, Lexington, Ky.

[21] Appl. No.: 08/675,090

[22] Filed: Jul. 3, 1996

[51] Int. Cl.⁶ .......................... C07H 19/00; C07H 21/04; C13N 15/00; A01G 1/00

[52] U.S. Cl. ...................... 536/22.1; 536/23.6; 536/24.1; 536/24.2; 435/440; 435/468; 435/240.1; 800/200; 800/205

[58] Field of Search .............................. 435/172.1, 240.1, 435/440, 468; 800/200, 205; 536/22.1, 23.6, 24.1, 24.2

[56] References Cited

U.S. PATENT DOCUMENTS

| | | | |
|---|---|---|---|
| 5,106,739 | 4/1992 | Comai et al. | 435/172.3 |
| 5,145,783 | 9/1992 | Kishore et al. | 435/320.1 |
| 5,164,316 | 11/1992 | McPherson et al. | 435/240.4 |
| 5,242,412 | 9/1993 | Blake, III | 604/167 |
| 5,304,730 | 4/1994 | Lawson et al. | 800/205 |
| 5,378,619 | 1/1995 | Rogers | 435/172.3 |
| 5,463,175 | 10/1995 | Barry et al. | 800/205 |
| 5,503,999 | 4/1996 | Jika et al. | 435/172.3 |
| 5,510,253 | 4/1996 | Mitsky et al. | 435/172.3 |
| 5,512,466 | 4/1996 | Klee et al. | 435/172.3 |

FOREIGN PATENT DOCUMENTS

WO94/24848 11/1994 WIPO.

OTHER PUBLICATIONS

Indu B. Maiti et al., "Plants that express a potyvirus proteinase gene are resistant to virus infection", Proceedings of the National Academy of Sciences, Jul. 1, 1993, vol. 90, No. 13, pp. 6110–6114.

Indu B. Maiti et al., "Promoter/leader deletion analysis and plant expression vectors with the figwort mosaic virus (FMV) full length transcript (FLt) promoter containing single or double enhances domains", Transgenic Research 6(2) pp. 143–156 1997.

G. Jason Smith et al., "Expression of Heterologous Genes Following Electroporation of the Marine Diatom *Skeletonema Costatum*", Plant Physiology, Abstract 803, Jun. 1995, vol. 108, No. 2.

Bird et al., "Transgenic Plants With Increased Solids Content", Chemical Abstracts, vol. 119, Abstract No. 19725In, 1993, p. 260.

Franklin et al., "High Expression of a Foreign Gene in Transformed Bean Callus", In Vitro Cellular & Development Biology, Mar. 19, 1992, vol. 28, No. 2, Abstract P–1119.

Rie Terada et al., "Expression of CaMV35S–GUS gene in transgenic rice plants", Molecular & General Genetics, vol. 220, pp. 389–392, 1990.

Ricky Yeargan et al., "Tissue partitioning of cadmium in transgenic tobacco seedlings and field grown plants expressing the mouse metallothionein 1 gene", Transgenic Research 1, 261–267 (1992).

Indu B. Maiti et al., "Properties of transgenic plants that express a functional potyvirus P1 proteinase gene", 1995, pp. 1–18.

(List continued on next page.)

Primary Examiner—Ardin H. Marschel
Assistant Examiner—Jezia Riley
Attorney, Agent, or Firm—McDermott, Will & Emery

[57] ABSTRACT

Use of wild type and modified viral FLt promoters of FMV in the expression of chimeric genes in plant cells. The FLt promoter from FMV is modified with duplicated enhancer domains. The FLt promoter with its single or double enhancer domains is linked to heterologous coding sequences to form chimeric gene constructs. These genes have been shown to be expressed well in plant cells.

12 Claims, 17 Drawing Sheets

OTHER PUBLICATIONS

Indu B. Maiti et al., "Properties of transgenic plants that express a functional potyvirus p1 proteinase gene or a fused CP gene", 8th International Congress Molecular Plant–Microbe Interactions, Jul. 14–19, 1996, (Abstract # B–78).

Indu B. Maiti et al., "Expression of the Tobacco vein mottling virus nuclear inclusion protein (NIa) gene in tobacco", J. Cell. Biochem. Supplement 16F, (Abstract # Y213).

Indu B. Maiti et al., "Seed–Transmissable Expression of Mammalian Metallothionein in Transgenic Tobacco", Biochemical and Biophysical Research Communications, vol. 150, No. 2, 1988, pp. 640–647.

Indu B. Maiti et al., "Expression of the Tobacco Vein Mottling Virus Coat Protein (CP) and Cylindrical Inclusion Proteion (C1) Genes in Tobacco", 3rd International Congress Int. Soc. Plant Mol. Biol. meeting Oct. 6–11, 1991 (Abstract # 1154).

Indu B. Maiti et al., "Plants that Express a Potyvirus Proteinase Gene are Resistant to Virus Infection", Proc. Natl. Acad. Sci., vol. 90, pp. 6110–6114 (1993).

Indu B. Maiti et al., "Light Inducible and Tissue–Specific Expression of a Chimeric Mouse Metallothionein cDNA Gene in Tobacco", Plant Science, 76 (1991) pp. 99–107.

Indu B. Maiti et al., "Inheritance and Expression of the Mouse Metallothionein Gene in Tobacco", Plant Physiol. (1989) 91, pp. 1020–1024.

Indu B. Maiti et al., "Developing Genetically Engineered Disease, Pest and Herbicide Resistance in Tobacco", Recent Advances in Tobacco Science, vol. 18, Sep. 27–30, 1992, pp. 45–68.

Indu B. Maiti et al., "Multiple Potyvirus Genes do not Confer Protection Upon Plants Additively", 4th Congress of ISPMB meeting, Jun. 19–24, 1994 (Abstract # 1533).

Kiernan et al. Transformation and Regeneration of *Nicotiana Edwardsonii*. Plant Science. 1989, vol. 64, No. 1, pp. 67–78, see entire document.

FIG. 1A

```
-456
 ↓
AGAATTCTCAGTCCAAAGCCTCAACAAGGTCAGGTACAGAGTCTCCAAA    6530
         9a         9c    10d           11b    11a         9b
CCATTAGCCAAAGTACAGAGGATCAATGAAGATCTTCAATCAAAGTA     6580
                    7c                      8b
AACTACTGTTCCAGCACATCATGGTCAGTAAGTTTCAGAAAAAGAC      6630
            8a    7b        -284        7a
                             ↓3c
ATCCACCGAAGACTTAAAGTTAGTGGGCATCTTTGAAAGTAATCTTGTCA  6680
        -249      -238             5b        6b
         ↓           ↓3b
ACATCGAGCAGCTGGCTTGTGGGACCAGACAAAAAGGAATGGTGCAGA    6730
    -198           5a
     ↓6a
ATTGTTAGGCGCACCTACCAAAAGCATCTTGCCTTTATTGCAAAGATAA   6780
                 3a                  2b       2a
AGCAGATTCCTCAGTACAAGTGGGAACAAAATAACGTGAAAAGAGCT     6830
                                            1b      1a
GTCCTGACAGCCCCACTCACTAATGGTATGAGAACGCAGTGAGACCAC    6880
                                -73
                                 ↓
AAAAGAATTCCCTCTATATAAGAAGGCATTCATTCCCATTTGAAGGATCA  6930
         -47            +10
          ↑              ↑
TCAGATACTGAACCAATATTTCTCACTCTAAGAAATTAAGAGCTTTGTAT  6980
 ↑ → +1
```

TO FIG. 1B

FROM FIG. 1A

```
TCTTCAATGAGAGGCTAAGACCCTAAAGAGTTTCGAAAGAGAAATGTAGT         7030
                      ↑
                     +64
ATAGTAAGAGTCCTCCCAGTCCGGGAGATTGTAATAAAGAGATCTTGTAA         7080
TGGATCCAAGTGTCTGTAATTTTTGGAAAAATGATCTATAAAATATTCA          7130
       ↑
      +167
ATCTTTCTTAAGCTTATTCAAAGAACAAACATACTATCTATCATCCAAA          7180
    ↑
   +204
TCCACAGAGTGACAGAGAGAAAAATGGTCTGTGTTGTGTGGATCTGAAGTA        7230
                                              ↑
                                             +287
CCGCCGAGGCAGGAGGCCGTTAGGGAAAAAGGGACTGTTTGACCGTCAA          7280
AGTATCAGGCTGGCTCTAGGAAGGAAGATGAAGATATCAGGTATTGGTTT         7330
                 ↑
                +377
ATGTTCTAAAAAATAAGTAATAAAAAAGTTTATTAAAAAGAAAATT             7380
TTATCAAGAGCAAATTACATGTCTAGAGATACCTAGATCTATATTACAA          7430
TAATCTTACTTACATGTTTATTCGTGACTCTAAATTAAAAATGTTT             7480
AATTGTTTATTCAAAACAATGCCAGGACTAACCCTCCAGGAAGAGTATAT         7530
                                      ↑
ACTCTTAGCACACTTATTCTTCAGTGCTCGAAGAAGTCAAGCAGGTAC           7580
AACTGCATTCAGGAGACTTCCAGTCTCTCAGAAGTCTATATGCTAGCTT          7630
ACGGGCTTCGGTCACCAAGCTCATCTCCAAGCGAGAATTTCAGCTGT            7680
                                    ↑
                                   +736
```

FIG. 1B

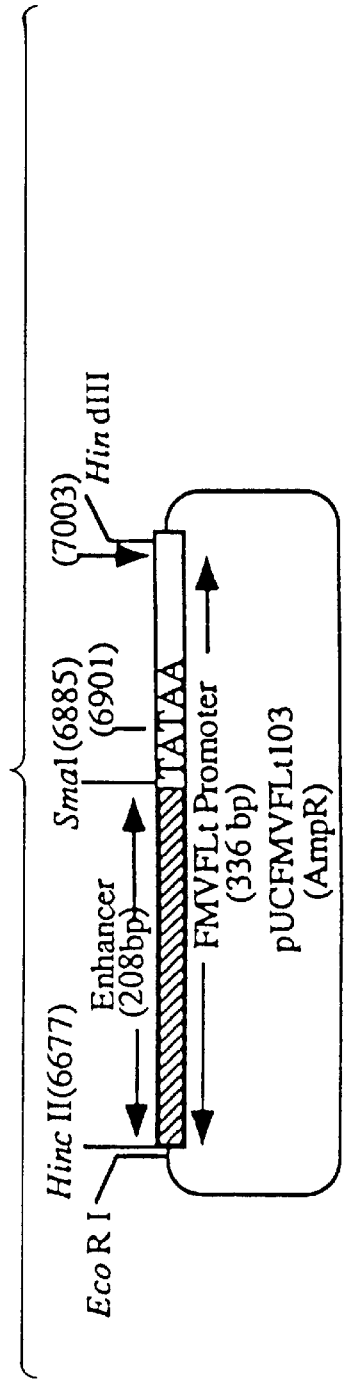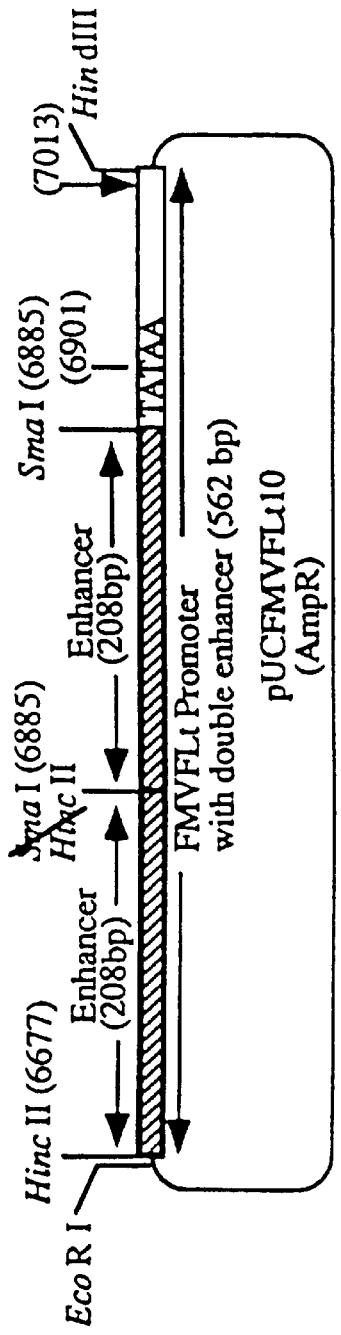
FIG. 2B

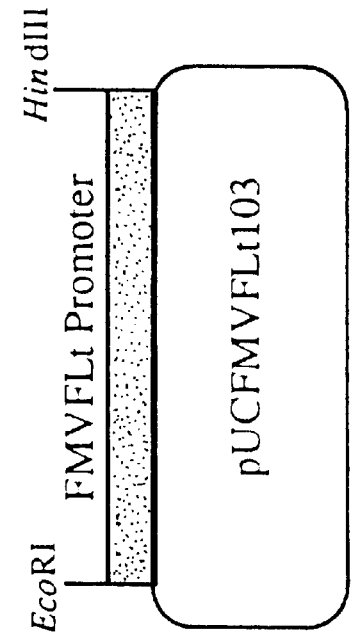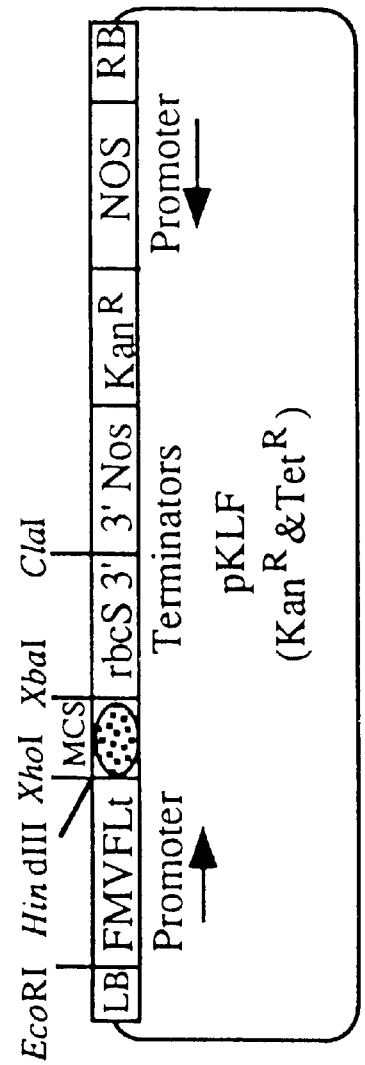
FIG. 4B

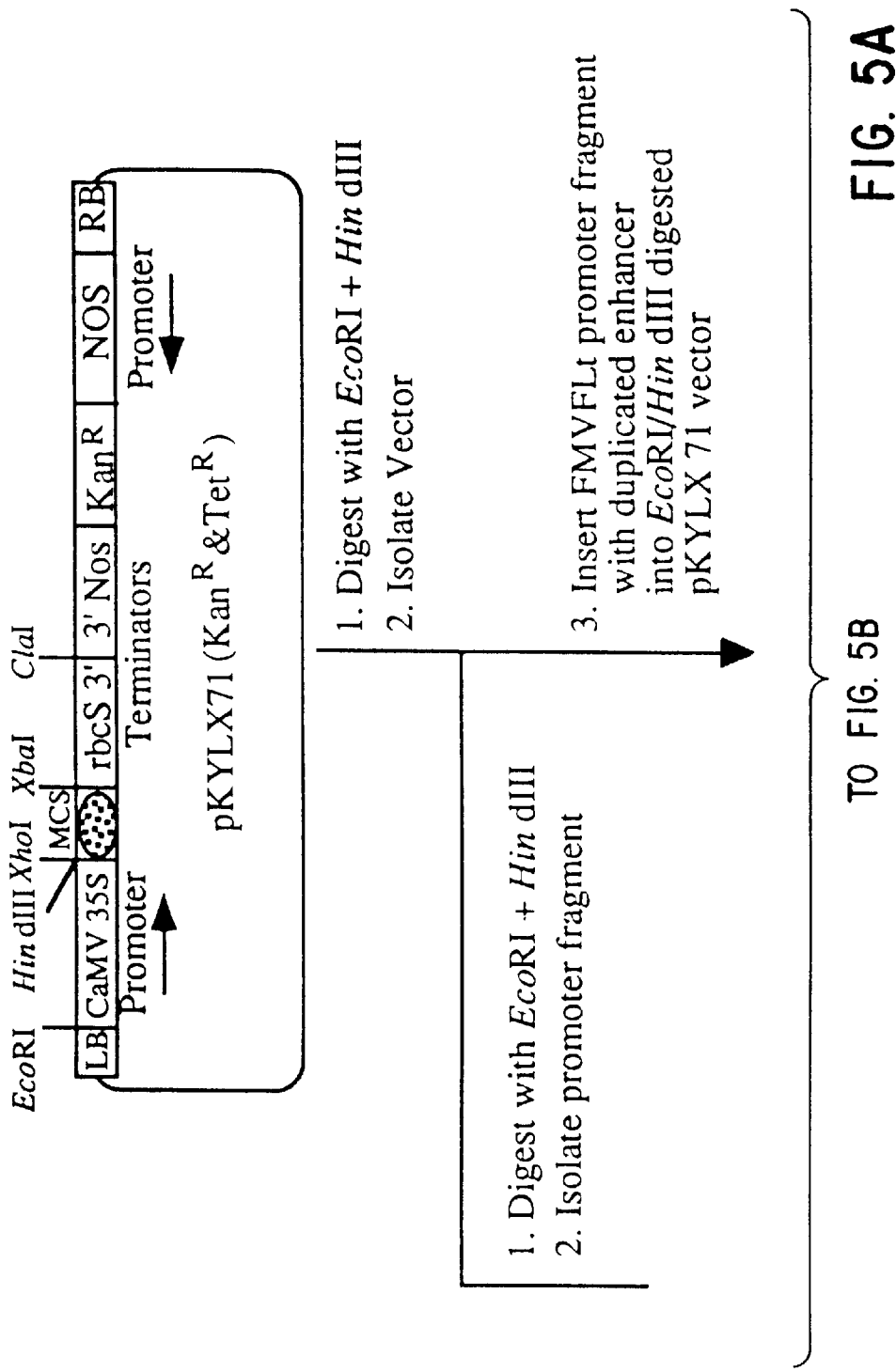

FROM FIG. 5A
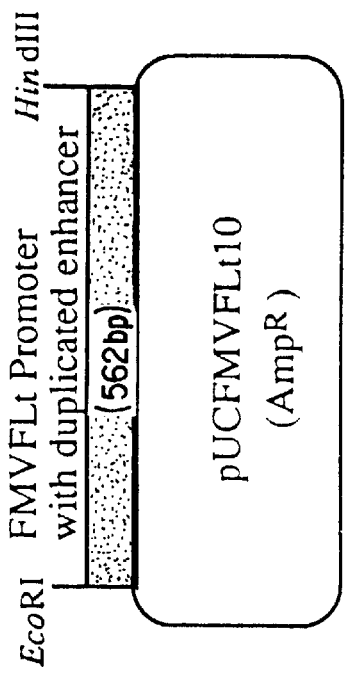
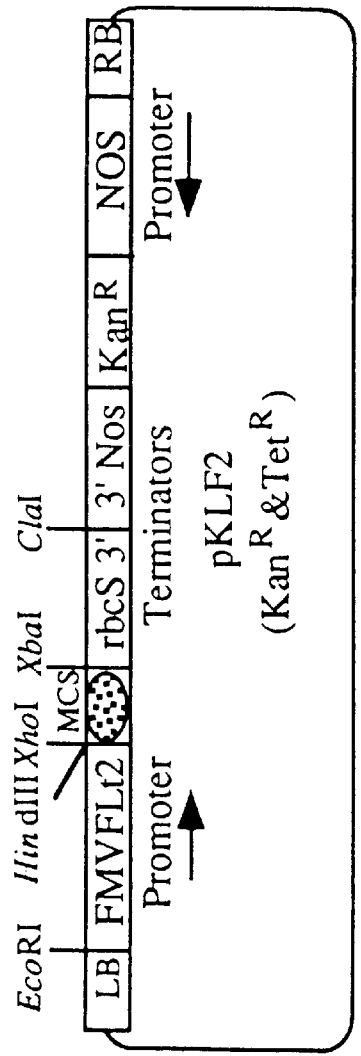
FIG. 5B

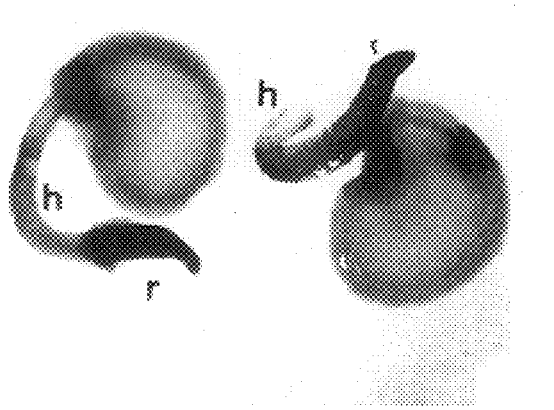
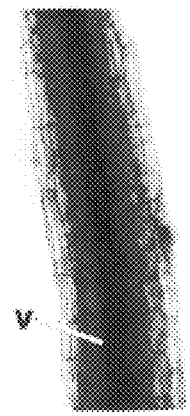
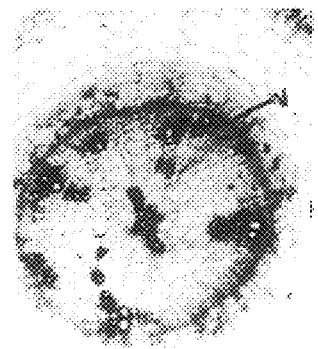
FIG.9J  FIG.9K  FIG.9L
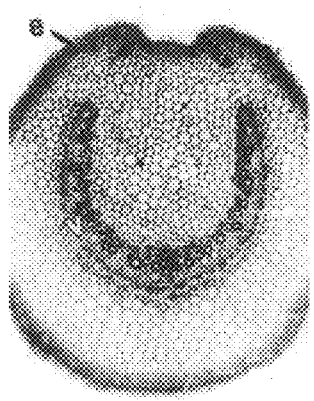
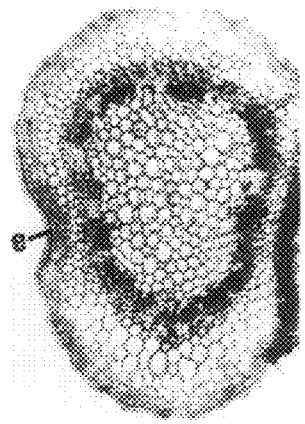
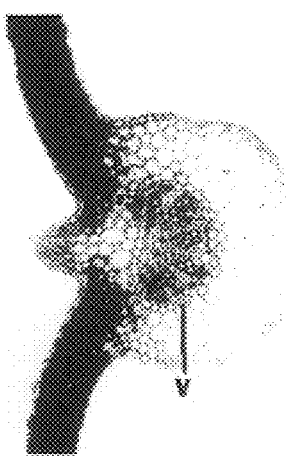
FIG.9M  FIG.9N  FIG.9O

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
GTGGAAAAAG                                                          10
```

(2) INFORMATION FOR SEQ ID NO:2:

(i) SEQUENCE CHARACTERISTICS:
        (A) LENGTH: 1199 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

```
AGAATTCTCA GTCCAAAGCC TCAACAAGGT CAGGGTACAG AGTCTCCAAA CCATTAGCCA     60
AAAGCTACAG GAGATCAATG AAGAATCTTC AATCAAAGTA AACTACTGTT CCAGCACATG    120
CATCATGGTC AGTAAGTTTC AGAAAAAGAC ATCCACCGAA GACTTAAAGT TAGTGGGCAT    180
CTTTGAAAGT AATCTTGTCA ACATCGAGCA GCTGGCTTGT GGGGACCAGA CAAAAAAGGA    240
ATGGTGCAGA ATTGTTAGGC GCACCTACCA AAAGCATCTT TGCCTTTATT GCAAAGATAA    300
AGCAGATTCC TCTAGTACAA GTGGGGAACA AAATAACGTG GAAAAGAGCT GTCCTGACAG    360
CCCACTCACT AATGCGTATG ACGAACGCAG TGACGACCAC AAAAGAATTC CCTCTATATA    420
AGAAGGCATT CATTCCCATT TGAAGGATCA TCAGATACTG AACCAATATT TCTCACTCTA    480
AGAAATTAAG AGCTTTGTAT TCTTCAATGA GAGGCTAAGA CCCTAAAGAG TTTCGAAAGA    540
GAAATGTAGT ATAGTAAGAG TCCTCCCAGT CCGGGAGATT GTAATAAAGA GATCTTGTAA    600
TGGATCCAAG TGTCTGTAAT TTTTGGAAAA ATTGATCTAT AAAATATTCA ATCTTTCTTT    660
AAGCTTATTC AAAGAACAAA CATACTATCT ATCATCCAAA TCCACAGAGT GACAGAGAGA    720
AAATGGTCTG TGTTGTGTGG ATCTGAAGTA CCGCCGAGGC AGGAGGCCGT TAGGGAAAAA    780
GGGACTGTTT TGACCGTCAA AGTATCAGGC TGGCTCTAGG AAGGAAGATG AAGATATCAG    840
GTATTGGTTT ATGTTCTAAA AAATAAGTAA TAAAGAAAAA AGTTTATTAA AAAGAAAATT    900
TTATCAAGAG CAAATTACAT GTCTAGAGGA TACCTAGATC TATATTACAA TAATCTTACT    960
TACATGTTTT ATTTCGTGAC TCTAAATTAA AAAATTGTTT AATTGTTTAT TCAAAACAAT   1020
GCCAGGACTA ACCCTCCAGC AAGAGTATAT ACTCTTAGCA CACCTTATTC TTCAGGTACT   1080
CGAAGAAGTC AAGCAGGTAC AACTGCATTC AGGAGACTTC CAGTCTCTCA GAAGTCTATA   1140
TGCTAGGCTT ACGGGCTTCG GTCACACCAA GCTCATCTCC AAGCGAGAAT TTCAGCTGT    1199
```

FULL LENGTH TRANSCRIPT (FLT) PROMOTER FROM FIGWORT MOSAIC CAULIMOVIRUS (FMV) AND USE TO EXPRESS CHIMERIC GENES IN PLANT CELLS

TECHNICAL FIELD

The present invention relates to the isolation, modification and use of wild type and modified viral FLt promoters of FMV in the expression of chimeric genes in plant cells. The FLt promoter from FMV is modified with duplicated enhancer domains. The FLt promoter with its single or double enhancer domains is linked to heterologous coding sequences to form chimeric gene constructs. These genes have been shown to be expressed well in plant cells. The FLt promoter with its double enhancer domain gives increased expression of genes compared to the FLt promoter with a single enhancer domain. This invention also includes plant cells, plant tissue, differentiated plants which express the chimeric genes of the invention.

BACKGROUND ART

A virus is a group of submicroscopic infective agents with double or single stranded DNA or RNA as core genetic material surrounded by a protein (and lipid in some case) shell called 'capsid' or 'coat'. It has no semipermeable membrane and it can multiply only in living cells using host cellular components. The short segment of the virus genetic material (FLt promoter) used in this invention can not infect plants or other organisms to cause disease. It is useful with selected foreign genes to obtain expression of these genes in other plants to confer useful properties to those transgenic plants.

Promoters from caulimoviruses

The following is a description of caulimoviruses also called plant pararetroviruses. Caulimoviruses derived their name from cauliflower mosaic virus (CaMV), the type member of the group (for reviews see Shepherd, 1989; Covey and Hull, 1992). More than a dozen types of caulimoviruses have been described to date. All have small circular DNA molecules as their genetic material. The genomes of CaMV (Gardner, et al., 1981) and four other members of this group, namely carnation etched ring virus (CERV), (Hull, et al., 1986), figwort mosaic virus (FMV), (Richins, et al., 1987) soybean chlorotic mottle virus (SoCMV), (Hasegawa, 1989), and peanut chlorotic streak virus (PClSV) (Richins, 1993; Richins, et al., 1995) have been fully sequenced. CaMV is a circular double stranded DNA virus with a genome size of approximately 8 kb. It is organized into seven open reading frames (genes) and two intergenic regions.

In the case of CaMV, the polypeptides corresponding to the six genes (I to VI) have been detected in infected cells and their functions have been identified. The cell-to-cell movement function (Thomas, et al., 1993; Ducasse et al., 1995), aphid-transmission factor (Daubert et al., 1983; Woolson, et al., 1983), minor capsid protein (Giband, et al., 1986), major capsid protein (Daubert, et al., 1982), reverse transcriptase (Takatsui, et al., 1992), and inclusion body protein (Odell and Howell, 1980) are associated with ORFs I to VI respectively. The gene VII protein was not detected in vivo (Wurch, et al., 1991). Its function is not clearly established. However a sequence located with this ORF of FMV is involved in translation of viral genes (Gowda, et al., 1991).

The viral genome is replicated through reverse transcription of the terminally redundant full length transcript (Bonneville and Hohn, 1993) by a virus encoded reverse transcriptase. Two major viral transcripts, known as 35S RNA and 19S RNA are synthesized exclusively from the minus strand DNA by the host RNA polymerase II (Odell, et al., 1981; Howell and Hull, 1978). The large intergenic region (L-IR) which resides between gene VI and VII, contains the promoter (35S) for the full length transcript which spans the entire viral genome (Dixon and Hohn, 1984; Scholthof, et al., 1992). The 35S RNA serve as template for minus strand DNA synthesis by viral gene V encoded reverse transcriptase (Gordon, et al., 1988). The small intergenic region (S-IR) residing between gene V and gene VI contains a promoter (19S) which transcribes gene VI only (Odell and Howell, 1980). The PClSV is apparently lacking the S-IR sequence, however both FMV (Scholthof, et al., 1992) and PClSV (Richins, 1993) have also been shown to have similar transcripts to the 19S and 35S RNA found in CAMV infected plant cells.

The CaMV 35S promoter, which spans about 941 base pair (bp) upstream from the transcription start site, has been shown to be active in various monocot and dicot cells. The cis-regulatory elements that are involved in directing transcription initiation reside within this region. The CaMV 35S promoter has a modular construction that includes an enhancer (Lam, 1994, and references there in) similar to those of other promoters like that of SV40 in mammalian systems (Ondek, et al., 1987; Schirm, et al., 1987; Fromental, et al., 1988). The 5' deletion analysis of CaMV35S promoter, studied in transformed tobacco calli or a protoplasts transient assay system, indicates that a promoter fragment of 343 bp upstream from the transcription start site is sufficient for high promoter activity (Odell, et al., 1985, Ow, et al., 1987).

The high CaMV35S promoter activity is the result of synergistic and combinatorial effects of enhancer elements residing in the −343 to −46 region upstream of the TATA element promoter (−46 to +8) (Fang, et al., 1989, Benfey, et al., 1989, Benfey and Chua, 1990, Benfey, et al., 1990a and Benfey et al., 1990b).

U.S. Pat. No. 5,378,619 to Rogers discloses a full length transcript promoter from the figwort mosaic virus. U.S. Pat. No. 4,940,835 to Shaw discloses the cauliflower mosaic virus 35S promoter. The latter patent claims chimeric plant genes containing the cauliflower mosaic virus promoter sequence. The patent does not disclose a double full length transcript promoter from the figwort mosaic virus in a transgenic plant and its expression advantages.

Several protein binding sequence motifs have been identified in the enhancer region of the 35S promoter (Lam, et al., 1989; Lam and Chua, 1989; Prat, et al., 1989; Bouchez, et al., 1989, Yanagisawa and Izui, 1992). Identical or similar sequence motifs are also present in promoters of other caulimoviruses (Bouchez, et al., 1989; Sanger, et al., 1990; Cooke and Penon, 1990; Richins, et al., 1993). Two nuclear binding protein factors, known as Activating Sequence Factor-1 and -2 (ASF-1 and ASF-2) from tobacco have been well characterized. ASF-1 binds to the activating sequence as-1 (−82 to −62) region of 35S promoter. Two TGACG motifs within this site are essential for DNA-protein interaction (Lam, et al., 1989). The as-1 motif is also found in full length transcript promoters from other caulimovirus including FMV (Sanger, et al., 1990, and present studies), PClSV (Richins, 1993) and MMV (Shepherd group, unpublished observation).

Single or multiple copies of enhancer sequences from the CaMV 35S promoter can increase homo- and heterologous promoter activity in an orientation-independent manner (Kay, et al., 1987; Ow, et al., 1987: Odell, et al., 1988; Fang, et al., 1989; Driesen, et al., 1993; Omirulleh, et al., 1993). The enhancement of promoter activity was proportional to the copy number of the enhancer sequence (Kay, et al., 1987; Ow, et al., 1987; Omirulleh, et al., 1993). Similar observation was made when single or multiple copies of the enhancer sequence was inserted upstream of the TATA element of the CaMV19S promoter (Ow, et al., 1987; Driesen, et al., 1993), rbcS-3A promoter (Fang, et al., 1989) and the nos promoter (Odel, et al., 1988).

U.S. Pat. No. 5,463,175 to Barry et al. discloses the figwort mosaic virus promoter. U.S. Patent No. 5,503,999 to Jilka et al. discloses the cauliflower mosaic virus 35S promoter and the figwort mosaic virus 35S promoter. U.S. Pat. No. 5,145,783 to Kishore et al. discloses the cauliflower mosaic virus 35S promoter. Figwort mosaic virus promoter is also disclosed.

U.S. Pat. No. 5,242,412 to Brown et al. discloses the figwort mosaic virus 35S promoter. U.S. Pat. No. 5,510,253 to Mitsky et al. discloses the figwort mosaic virus promoter. U.S. Pat. No. 5,512,466 to Klee et al. discloses the cauliflower mosaic virus 35S promoter and the figwort mosaic virus promoter.

U.S. Pat. No. 5,304,730 to Lawson et al. discloses the figwort mosaic virus 35S promoter. PCT Publication WO 94/24848 discloses a transgenic plant in which a chimeric gene comprising a wound inducible promoter which shows enhanced resistance to insect infection. Examples of vectors at least with a pKYLX4, pKYLX5 and pKYLX71 vectors.

U.S. Pat. No. 5,106,739 to Comai et al. discloses a caulimovirus 35S enhanced mannopine synthase promoter and method for using the promoter. The patent also discloses the use of a double CaMV 35S promoter in a construct used to create transgenic plants.

Proceedings of the National Academy of Sciences, Volume 90, page 6110–6114, July 1993, entitled "Plants that express a potyvirus proteinase gene are resistant to virus infection". This publication discloses pKYLX71:35S vector.

The Journal of Cellular Biochemistry, Supplement 16F, Apr. 3–16, 1992, discloses a binary vector PKYLX71-GUS. In Vitro Cellular & Development Biology, March 19, 1992, Volume 28, No. 3, Abstract P-1119 discloses PKYLX71-GUS vector. Molecular & General Genetics, Volume 220, page 389–392, Spring 1990, discloses expression of the caulimovirus 35S-GUS gene in transgenic rice plants.

Chemical Abstracts, Volume 119, Abstract No. 197251n discloses transgenic plants with increased solids content. The plants are made with a construct including a CaMV 35S promoter. Plant Physiology, June 1995, Volume 108, No. 2, discloses in Abstract 803, the expression of heterologous genes following electroporation of the marine diatom. Electroporation induced loading of plasmid CaMV35S.

The engineering of novel traits into plants and other crops promises to be an area of great agricultural importance (Maiti and Hunt, 1992; Wagner, 1992). Plant genetic engineering techniques allow researchers to introduce heterologous genes of interest into plants cells to obtain the desired qualities in the plants of choice. Plant genetic engineering has led to a rapid progress in production of economically valuable germplasm with improved characteristics or traits such as insect resistance, virus resistance, fungal resistance, herbicide resistance, bacterial or nematode pathogen resistance, cold or drought tolerance, improved nutritional value, seed oil modification, delayed ripening of fruits, and male sterility, to name a few.

These newly created germplasms provide a enhanced development in breeding programs for crops improvement as well as a better understanding of gene regulation and organization in transgenic plants. The expression of useful foreign traits in plants is a major focus in plant biotechnology. Plant metabolic engineering is the application of genetic engineering methods to modify the nature of chemical metabolites in plants. For metabolic engineering where multiple genes need to be inserted into one cell, the use of different strong constitutive promoters is desirable in order to avoid genetic instability caused by recombination between identical or closely related promoter sequences taken from plants themselves. Through use of the present promoter sequence the introduced genes can be transcribed to messenger RNA and then translated to resultant proteins to exhibit new traits or characters.

Besides developing useful traits in crops, the present invention provides a further understanding of molecular pathways involved in disease development and secondary metabolism in plants. Moreover, by engineering plants with specific foreign genes, the responses of plants to abiotic and biotic stress and stress related metabolism can be analyzed. The invention described herein in developing gene vectors with newly defined promoters of the caulimoviruses advances this effort.

A wide variety of well-characterized genes of animal, human, bacterial and of plant origin, including those of several viruses, are available for engineering plants. For the most effective expression of this wide selection of genes either constitutive or regulated, versatile gene expression vectors are required. At the University of Kentucky, Dr. Arthur Hunt and his colleagues have developed a series of plant expression vectors (Schardl, at al., 1987) with a constitutive 35S promoter from cauliflower mosaic virus (CaMV) which have been successfully used to produce transgenic plants (Maiti, et al., 1988, 1989, 1991, 1993, 1994, 1995; Graybosh, et al., 1989; Berger, et al., 1989; Yeargan, et al., 1992; Liod, et al., 1992).

The present invention, develops additional useful promoters from FMV for high level expression of foreign genes in transgenic tobacco. These vectors are useful for both direct DNA uptake by isolated protoplasts and Ti plasmid- mediated gene transfer.

Enhanced levels of transcription via highly active promoters are essential for high levels of gene expression. The most widely used promoter for plant transformation, as described earlier, has been the 35S promoter of CaMV. It is active in a wide variety of plants and tissues. It is also the most thoroughly characterized promoter with respect to the sequence elements active in its transcriptional activity (Benfey and Chua, 1990). Kay, et al., 1987 showed that the transcriptional activity of the CaMV 35S promoter could be increased approximately tenfold by making a tandem duplication of 250 base pairs of upstream sequence.

Similar observation have been made with other promoters (McNeall, et al., 1989). The present inventors have constructed and tested a construct with the FMV FLt promoter.

The Monsanto Co. has recently patented 35S and the 19S promoters of CaMV, and the full length transcript promoter from FMV. In both cases cloned DNA material was provided to Monsanto Co. by the present investigator, Dr. Shepherd, University of Kentucky, Lexington, Ky. The present inventors have overcome the deficiencies of prior transgenic plant promoters and have now developed new, unique promoters of equal or better expression strength.

SUMMARY OF THE INVENTION

The present inventions are applicable to plant genetic engineering. Specifically, the present inventions relate to the promoters from figwort mosaic virus and these promoters direct the expression of genes in plant cells.

Thus an object of the present invention is to provide a plasmid comprising a chimeric gene comprising a full length transcript (FLt) promoter and at least one enhancer domain of the figwort mosaic virus (FMV), operably linked to a heterologous gene sequence which is heterologous to said promoter.

Another object of the invention provides a plasmid with a single, a double, or multiple enhancer domains. In a preferred embodiment the plasmid of claim 1, further comprises a 5' non-translated leader sequence from figwort mosaic virus. The plasmid may optionally include a region of homology to an *Agrobacterium tumefaciens* vector and a T-DNA border region from *Agrobacterium tumefaciens*, wherein said chimeric gene is located between the T-DNA border and the region of homology. Examples of plasmids of the invention include intermediate plasmids pUCFMV FLt 10, PUCFMV Flt 101, PUCFMV Flt 102, and PUCFMV Flt 103.

In a preferred embodiment the plasmid full length transcript (Flt) promoter consists of the 3' portion of gene VI and the intergenic region including nucleotides 6481 to 7030 of the FMV genome. The heterologous gene is preferably downstream from the promoter and is capable of being expressed in a transgenic plant.

In an additional embodiment the plasmid comprises a) a FMV FLt promoter with single enhancer domain; b) a 3' nontranslated polyadenylation sequence of rbcS E9 gene; and (c) a structural sequence encoding neomycin phosphotransferase II.

Still another object of the invention is to provide for an expression vector comprising a chimeric gene including a full length transcript (FLt) promoter and at least one enhancer domain of the figwort mosaic virus (FMV), operably linked to a heterologous gene sequence which is heterologous to the promoter.

The expression vector may comprise a disarmed plant tumor inducing plasmid of *Agrobacterium tumefaciens*, and is preferably selected from pKLF, pKLF2, pKLF2-GUS, pKLF2-CAT, pKLF20-GUS.

The invention also provides for a plant cell transformed with the plasmid comprising a chimeric gene comprising a full length transcript (FLt) promoter and at least one enhancer domain of the figwort mosaic virus (FMV), operably linked to a heterologous gene sequence which is heterologous to said promoter.

Transgenic plants comprising the plasmid are also within the scope of the invention. Transgenic plants are preferably selected from crop plants including, but not limited to cotton, soy bean, alfalfa, oilseed rape, flax, tomato, sugar beet, sunflower, potato, tobacco, maize, wheat, rice, lettuce and banana plants. Any crop plant which is modifiable with the plasmid of the invention is included within the scope of this application.

The heterologous gene is expressed in plant tissues including but not limited to plant tissues selected from calyx, filament, pedicel, style, ovary, corolla, anther, stigma, leaf, stem, embryo, seed and root tissues.

The invention provides for a chimeric gene or DNA which is transcribed and translated in plant cells, said chimeric gene comprising a region comprising an FMV FLt promoter and at least one enhancer domain, wherein said region is free of a FMV protein-encoding DNA sequence and a DNA sequence which is heterologous the promoter.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF DRAWINGS

FIGS. 1A and 1B. The DNA sequence of the full length transcript (FLt) promoter from the figwort mosaic virus (FMV) strain DxS (Richins et al., 1987). The nucleotide sequence (FMV coordinates 6481 to 7680, a 1200 bp fragment) includes the 3' end of gene VI, and part of the large intergenic region, presented in the 5' to 3' direction of the transcript from left to right.

FIGS. 2A and 2B. Construction strategy of FMV FLt promoter with its single and double enhancer domains. Number in parenthesis indicate nucleotide position in the FMV genome.

FIGS. 4A and 4B. Physical map of pKLF.

FIGS. 5A and 5B. Physical map of pKLF2.

STATEMENT OF DEPOSIT

Figure 2A:
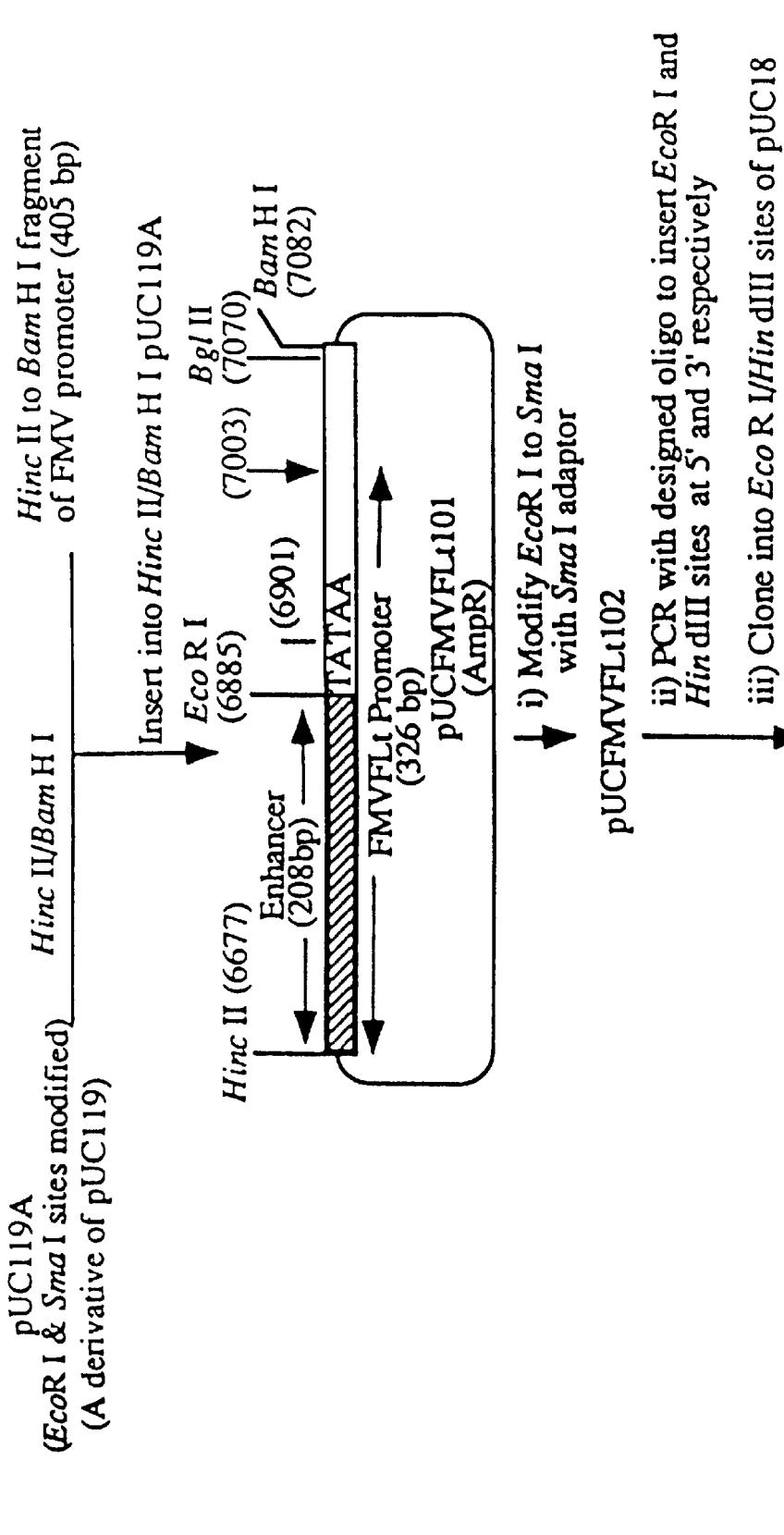

Plasmids pKLF and pKLF2 in *E. coli* TB1 have been deposited with the Agricultural Research Service (ARS) Patent Culture Collection (NRRL), 1815 North University Street, Peoria, Ill., USA, 61604, under the terms of the Budapest Treaty on Jun. 28, 1996. The deposit will be maintained for the life of the patent as required by Treaty. The recombinant bacteria may be cultured in LB medium in the presentce of tetracycline (15 µg/ml).

DESCRIPTION OF THE INVENTION

The present invention includes: i) isolation of the promoter for the full length transcript (FLt) from figwort mosaic virus (FMV) strain DxS (Richins, et al. 1987) from the full length viral DNA clone as described below in Experimental Section. The modification includes duplication or multimerization of the enhancer domain of the FLt promoter from FMV. The FLt promoter sequence for FMV is shown in FIG. 1.; iii) Use of FMV promoter in a method for transforming plant cells, expression vectors including FMV promoter, a chimeric gene including FMV promoter sequence and transgenic plants, plant cells and seeds incorporating the FMV promoter in a chimeric gene.

The chimeric gene may preferably be composed of a promoter region, a 5' non-translated leader sequence the structural gene itself and a 3' polyadenylation sequence. The promoter is a DNA fragment composed of modular sequence which directs and regulates the expression of genes through transcription to messenger RNA. The proper regulatory signals/enhancer elements must be present in defined location in order to express the inserted gene into RNA and a resultant protein. The 3'-polyadenylation sequence is a non-translated region which signals the adenylation of the 3' end of the RNA in order to stabilize the RNA in the cytoplasm for subsequent translation into protein.

Certain promoters have a specific modular sequence which makes it either tissue specific, developmentally regulated or environmentally regulated for its selective expression of genes in cells. Promoters capable of directing RNA synthesis at higher rates compared to other promoters are desirable for many purposes. If these promoters are able to direct the expression of genes in most of tissues of plants, they are defined as constitutive promoters. The inventors have found that the CaMV 35S promoter is one of the strongest constitutive promoters. The transcriptional activity of the CaMV 35S promoter is the result of synergistic and combinatorial effect of enhancer elements residing upstream of the TATA element. Single or multiple copies of enhancer sequences from the CaMV 35S promoter can also increase homo- or heterologous promoter activity in an orientation-independent manner. The enhancement of promoter activity has been found to be related to the copy number of the enhancer sequence.

The inventors have developed expression vectors with the FMV promoter with its single and duplicated enhancer domains. The upstream enhancer elements of the strong constitutive promoter from the full length transcript of FMV has been doubled in a strategy to even further strengthen this promoter. Promoters from other caulimoviruses such as FMV, PCISV, and MMV as well as the better characterized CaMV 35S promoter will be useful for plant genetic engineering. The inventors have developed plant expression vectors with constitutive FLt promoters of FMV.

The primary objective of the present invention is to provide several strong and constitutive promoters to be used for expression of chimeric genes in transgenic plants. Another object of the present invention is to develop a strategy to further strengthen the promoters from the full length transcript of other member of the calimovirus (plant pararetrovirus) including FMV.

Experimental Procedures

Strains of FMV adapted to solanaceous plants have been described by Shepherd et al., 1987. Isolation of the promoter for the full-length RNA transcript (FLt) and characterization of its activity in protoplasts of tobacco has also been done in this laboratory (Gowda et al., 1889). The clone of the promoter (plasmid pFMV 20) was shown to give high levels of constitutive expression in tobacco cells (Gowda, et al., 1989). Later the FMV FLt promoter was shown to control transcription of an RNA transcript spanning the entire circular genome of FMV (Scholthof, et al., 1992); (Cooke, 1990). Another newly described caulimovirus PCISV (Reddy, et al., 1993; Richins et al., 1993) has been partially characterized in this laboratory. These investigations provide the materials (DNA clones) for the invention described herein.

Creation of plant expression vectors pKLF, pKLF2
Construction of a FMV FLt promoter with single and duplicated enhancer elements and creation of plasmids pKLF and pKLF2

The construction strategy for isolating the FMV FLt promoter and its enhancer domain is shown in FIG. 2. For the FLt promoter, a 406 bp Hinc II to Bam HI fragment (coordinates 6677 to 7082 of the FMV genome) was cloned into the corresponding sites of pUC119A (a modified pUC119 in which Eco RI and Sma I sites were destroyed by digesting with Eco RI and Sma I followed by ligation). The resulting plasmid was designated as pUCFMV FLt101. An Eco RI site located 6 bp upstream from the TATAA box was changed to a Sma I site using a Sma I adaptor. This change inserted 8 additional nucleotides (5'-ACCCGGGC-3') into the promoter sequence. The resulting plasmid was designated as pUCFMVFLt102. In the FLt promoter with its single enhancer domain, a 335 bp segment (position 6677 to 7003 of the FMV sequence) was amplified from pUCFMVFLt102 by PCR using appropriately designed oligonucleotides to insert an Eco RI at the 5' end and a Hin dIII site at the 3' end of the fragment. This promoter fragment was cloned into pUC18 at its Eco RI and Hin dIII sites. The resulting plasmid was designated pUCFMVFLt103.

Figure 3:
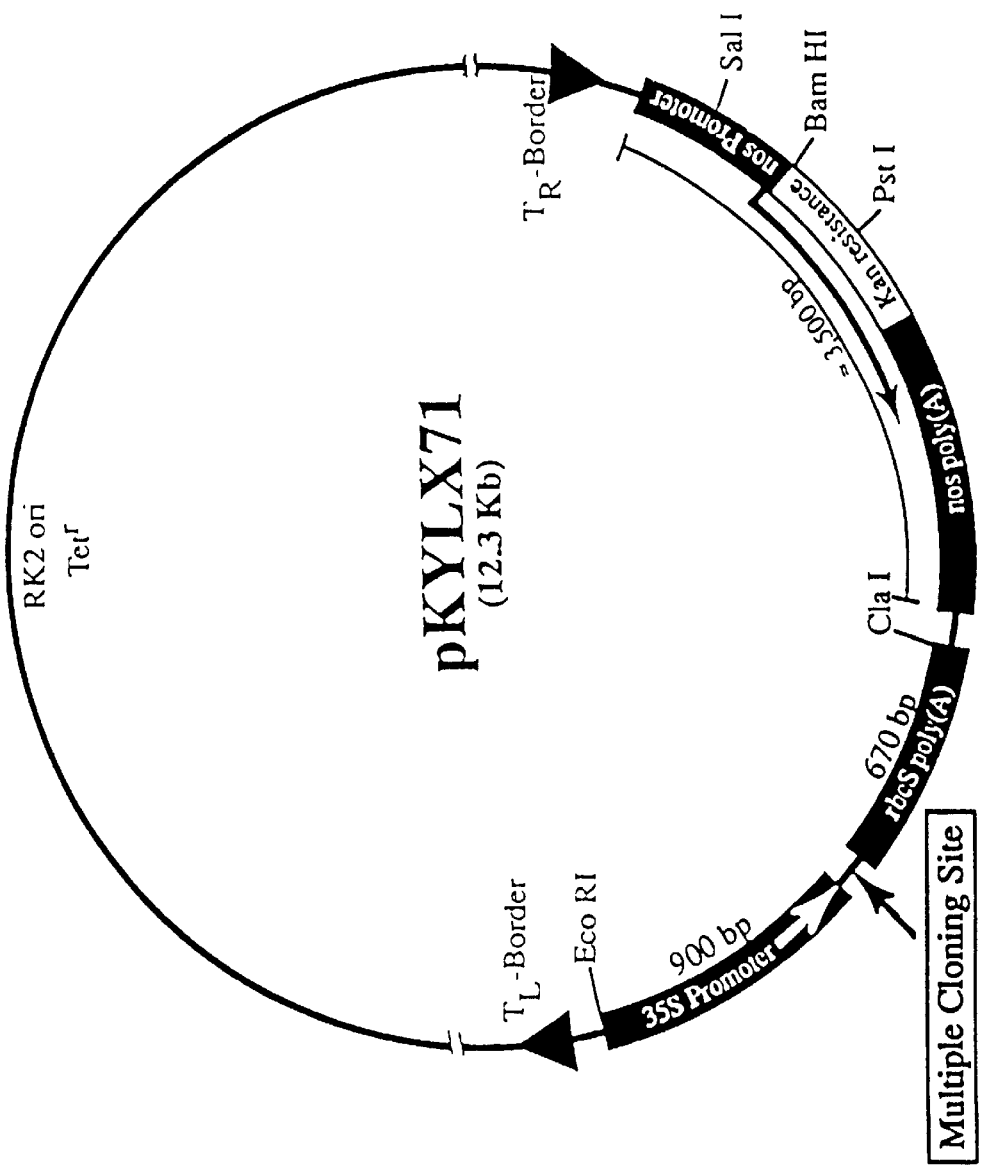
FIG. 3. Physical map of pKYLX71.

The enhancer domain Eco RI to Sma I fragment of 213 bp was isolated from pUCFMVFLt103 and this fragment was cloned into the Eco RI and Hinc II sites of pUCFMVFLt103, the resulting plasmid named pUCFMVFLt10 contains the FLt promoter with its duplicated enhancer domain. The FLt promoter sequence with either single or double enhancer domains was inserted into a plant expression vector by substituting it for the CaMV35S promoter of pKYLX71 (Schardl et al., 1987). The physical map of pKYLX71 is shown (FIG. 3). The unique Eco RI and Hin dIII sites that flank the promoter were used for this purpose. The resulting expression vectors were designated as pKLF (FIG. 4) when a single enhancer domain was present or pKLF2 (FIG. 5) when a double enhancer domain was present. These plasmids have multiple cloning sites (MCS: 5'-Hin dIII, Bam HI, Xho I, Pst I, Sac I and Xba I-3') with the following unique sites: Hin dIII, Xho I, Sac I and Xba I.

Testing the Expression Vectors with a GUS or CAT reporter gene: Stable transformation and analysis of transgenic plants The reporter genes CAT or GUS were tailored by PCR to include just the coding sequence with the initiation and termination codons of each gene, flanked by a Xho I site at the 5' end and a Sst I site at the 3' end. The PCR isolated fragment for the reporter gene (CAT or GUS) was digested with Xho I and Sst I, gel purified and cloned into the corresponding sites of plant expression vectors pKLF or pKLF2. The resulting constructs #109-CAT, 110-GUS, 111-CAT and 112-GUS (FIG. 6 B) were introduced into Agrobacterium tumefaciens strain C58C1:pGV3850 by triparental mating and tobacco (cv. Samsun NN) was transformed with the engineered Agrobacterium as described earlier (Maiti et al., 1993).

The construct #102 in pKYLXF20GUS contains an Eco RI to Hind III fragment from pF20GUS cloned into Eco RI/Hind III sites of pKYLX7 by replacing the CaMV 35S promoter flanked by Eco RI and Hind III sites.

To examine the integration of genes in transgenic plants, genomic DNA was isolated following the procedure (Thomson and Henry 1993) for PCR analysis. The integration of reporter CAT or GUS gene in the genome of transgenic plants (R0 and R1 progeny) was detected by PCR amplification using appropriately designed oligonucleotides specific for the CAT or GUS gene sequence. Specificity of each PCR product was tested by Southern hybridization with a GUS or CAT probe.

EXAMPLE 1

Figure 6A:
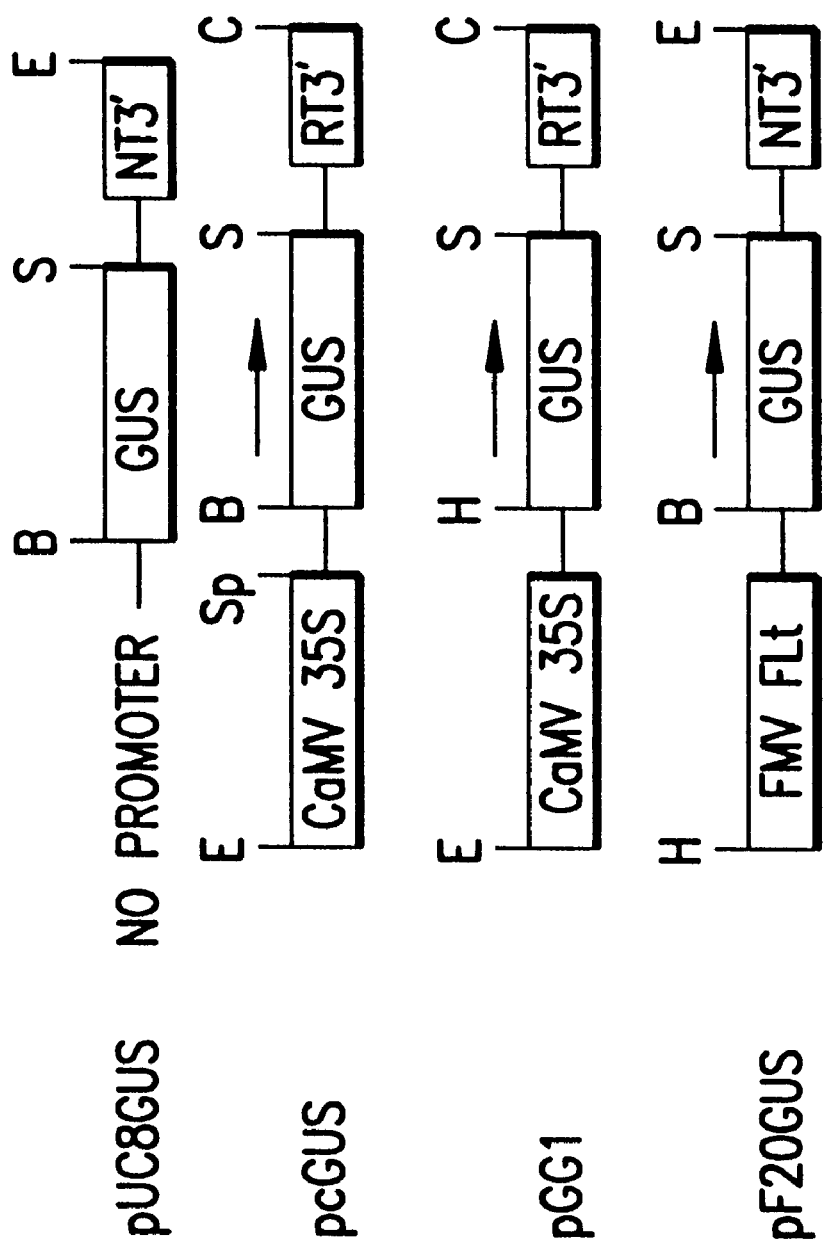
FIGS. 6A and 6B. Schematic representation of chimeric GUS or CAT constructs used for assaying promoter activity in transient expression analysis (A) and transgenic plants (B).

Comparative functional analysis of the CaMV35S and the FMV FLt promoters in transient expression experiments using tobacco leaf protoplasts. To compare the relative strengths of the CaMV 35S and the FMV FLt promoters, we tested different vector constructs with the GUS gene in transient expression experiments in protoplasts of *Nicotiana edwardisonii*. The schematic maps of the plasmids used in these experiments are shown in FIG. 6A. Isolation of protoplasts from *Nicotiana edwardsonii* cell suspension cultures and electroporation of protoplasts with supercoiled plasmid DNA containing CAT or GUS has been described (Gowda et al., 1989; Kiernan et al., 1993). In brief, an aliquot containing 2×106 protoplasts was electroporated with 50 μg of plasmid DNA. After 20 hrs, 2×105 protoplasts were harvested for each CAT or GUS assay. CAT activity was determined according to the published method (Gorman et al., 1982).

Plant tissue extracts containing 5 μg of soluble protein were used for each CAT assay. The reaction was carried out at 37° C. for 30 min. The rates of reaction were in a linear range over the period of incubation. Fluorometric GUS assays to measure GUS activity of plant tissue extracts and histochemical GUS assays to determine the distribution of GUS activity in plants on embryos and seedlings, were performed according to published procedure (Jefferson et al.,1987) . Protein in plant extracts was estimated (Bradford 1976) using BSA as a standard.

For the fluorometric assays, samples were homogenized in GUS extraction buffer (50 mM NaPO4, pH 7.0, 10 mM β-mercaptoethanol, 10 mM Na2 EDTA, 0.% Na Sarkosyl, 0.1% Triton X-100), and centrifuged for 10 min. at full speed in a microcentrifuge. Soluble protein (5 μg) from transgenic plant tissue extracts were incubated with 4-methyl umbelliferyl glucuronide (MUG) solution for 10 to 20 minutes after which fluorescence was measured. The activity remained linear with added enzymes. Fluorescence of a solution of 100 pmol 4-methyl umbelliferone (MU) in 0.2 M sodium carbonate was used for calibration. Fluorescence was measured on a minifluorometer (Model No TKO 100: Hoefer, San Francisco, Calif.), with an excitation wavelength of 365 nm and photodetector wavelength of 460 nm.

The results from the transient expression experiments are shown in Table 1. The gene constructs with the wild type FLt promoter (pFMV 20 GUS) with its single enhancer domain showed about 2.5 fold higher promoter activity than the CaMV 35S promoter-GUS construct (pGG1) in these assays. A control plasmid pc-GUS (CaMV 35S promoter-GUS-nos3' terminator) contains an extra out of frame ATG codon (as Sph I site GCATGC) in the multiple cloning site of pKYLX 7. The presence of this ATG codon causes about 7–8 fold less GUS activity compared to pGG1. The duplication of FMV FLt promoter enhancer domain in plasmid pKLF2-GUS increased the level of GUS activity about 4 fold as compared to pKLF-GUS with the single enhancer domain. This increase was also observed in a stably transformed system in intact tobacco plants. In pFMV 20 GUS, the FLt promoter with an Eco RI site located 6 bp upstream from the TATAA box was changed to a Sma I site using a Sma I adaptor. This change inserted 8 additional nucleotides (5'-ACCCGGGC-3') into the promoter sequence in pKLF-GUS.

EXAMPLE 2
Analysis of FMV FLt promoter activity in transgenic plants

Figure 6B:
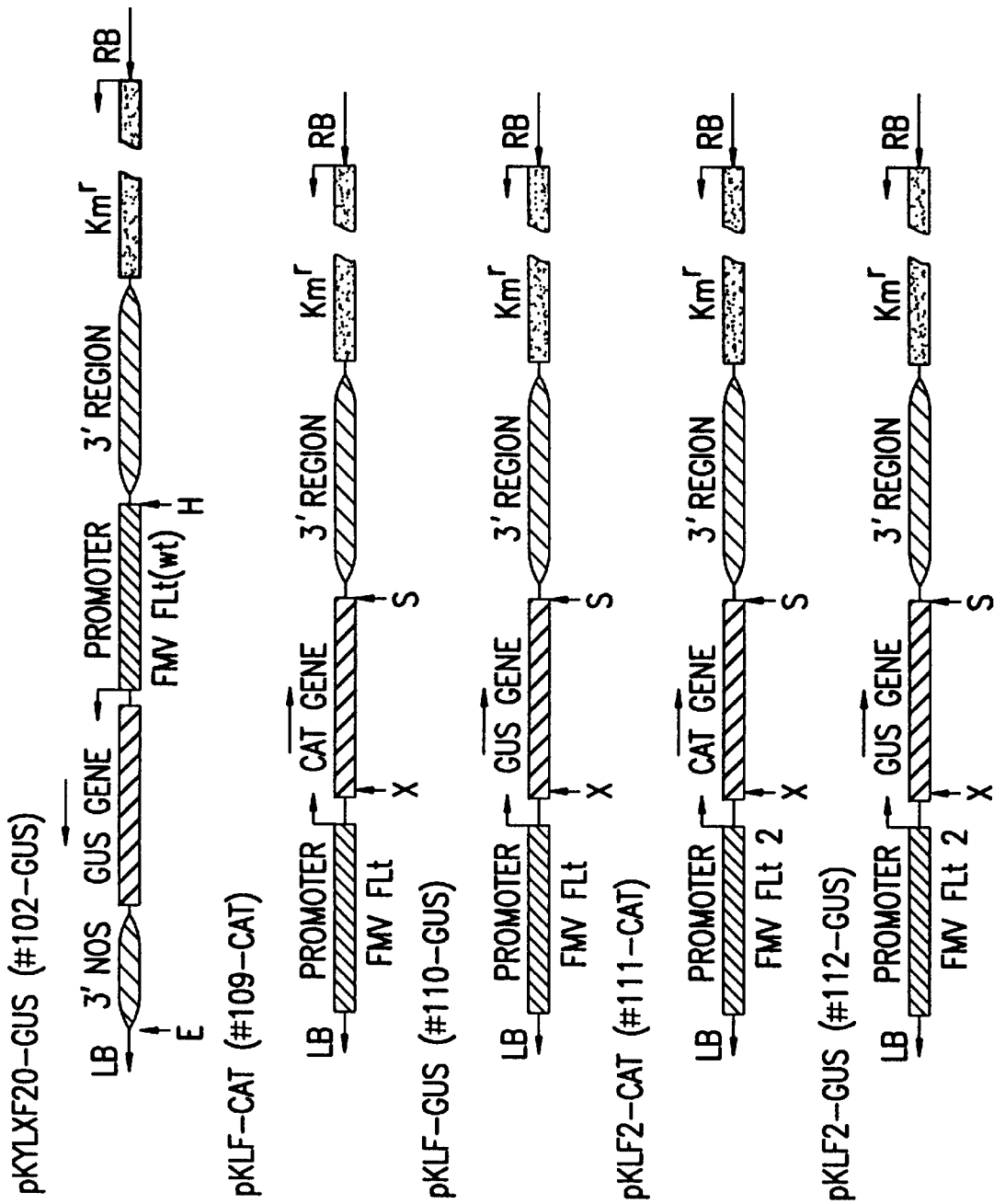

The constructs shown in FIG. 6 B were transformed into tobacco plants via the Agrobacterium co-cultivation method as described in Maiti et al., 1988. Transformations were done using *Nicotiana tabacum* cv Samsun NN or *Datura inoxia*. For screening of transformants tobacco plants arising from first generation seeds (R1 progeny), germination was done in presence of kanamycin (200 μg/ml). Primary transformants of tobacco were selected for resistance to kanamycin (300 mg/ml) and these were grown to maturity in the greenhouse. At least 8 to 10 independent lines were generated for each construct tested. The presence of the reporter genes, CAT or GUS, in genomic DNA from these transformants was detected by PCR amplification using primers based on sequences from the coding region of each gene. The specificities of PCR fragments were tested by Southern hybridization with CAT or GUS probes for the respective transformants (data not shown).

Figures 7A, 7B:
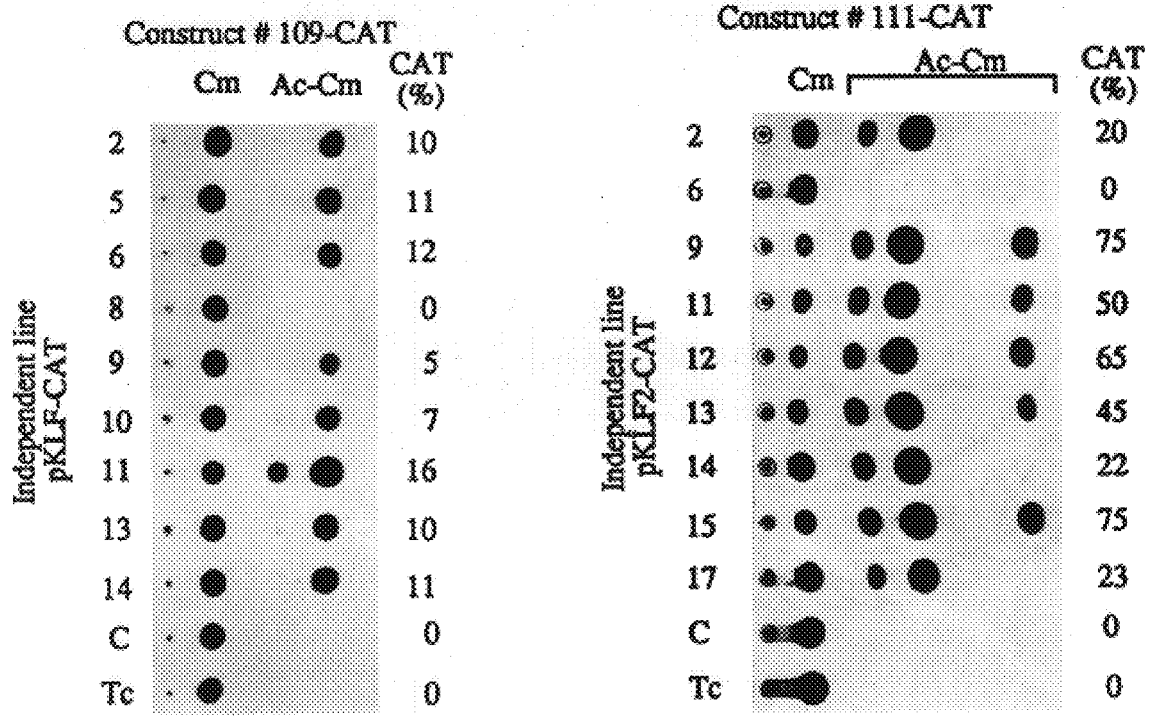
FIGS. 7A and 7B. FMV FLt promoter activity in transgenic plants expressing a CAT reporter gene.

The expression levels of the CAT reporter gene in independent transformants developed for pKLFCAT, pKLF2CAT are shown in FIG. 7 A & B. Individual plant lines generated from independent calli expressing the same gene showed variable CAT activity. Similar patterns of plant-to-plant variations in gene expression have been reported with many other plant promoters. It is believed that these variations are largely due to the difference in position of the integrated genes in the chromosome and the degree of co-suppression. Separate plant lines developed with pKLF2CAT showed more activity than any of the plants transformed with pKLFCAT. On average, about 4.5 fold higher activity was exhibited by plants transformed with pKLF2CAT, which has a duplicated enhancer domain, not present in plants transformed with pKLF-CAT which has a single enhancer domain.

Figure 8:
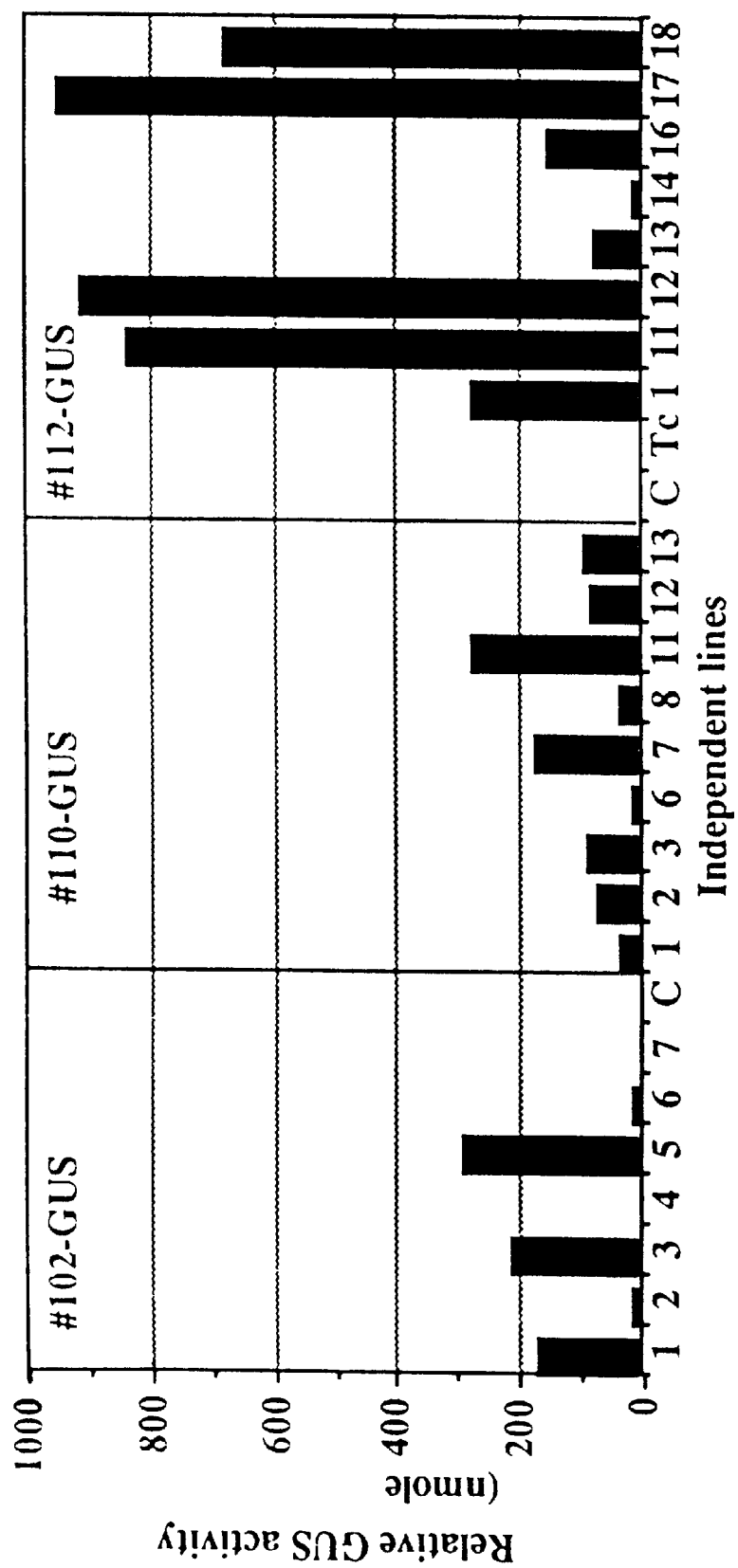
FIG. 8. A comparison of the wilds type and modified FMV Flt promoter activity in transgenic *Nicotiana tabacum* cv Samsun NN (R0 progeny) expressing a GUS reporter gene.
Figure 9A:
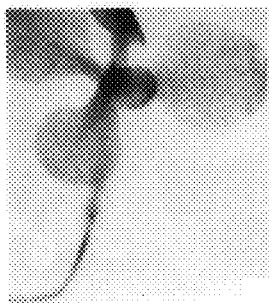
FIGS. 9A–9O. Histochemical localization of GUS activity in developing transgenic tobacco.
Figure 9B:
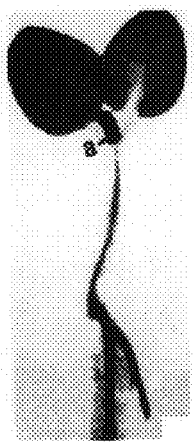
Figure 9C:
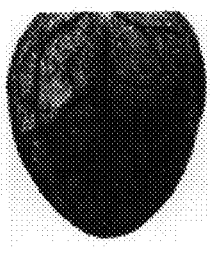
Figure 9D:
Figure 9E:
Figure 9F:
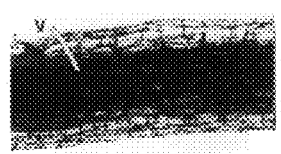
Figure 9G:
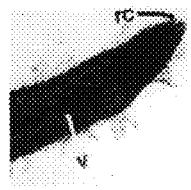
Figure 9H:
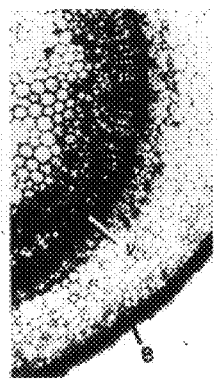
Figure 9I:
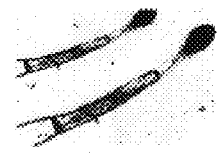

The wild type FMV FLt promoter in pKYLXF20GUS (construct #102) was compared with a modified FMV FLt promoter in pKLFGUS (construct #110) and pKLF2GUS (construct #112). The expression of the GUS reporter gene in leaf extracts of primary transformants is shown in FIG. 8. Although variation in GUS activity in transgenic tobacco plants was considerable, the GUS expression in leaves in plants transformed with PKYLX GUS, (construct #102-GUS) are very similar to that of plants transformed with pKLFGUS, which contains 8 additional base pairs just 6 bp upstream of TATA box (as a result of inserting a SmaI linker in its EcoRI site). Promoter activity was not affected by this insertion.

Although there is variability in GUS expression in several independent lines transformed with pKLF2GUS (construct #112), four lines had more activity (average of 3.5 fold greater activity) than any transformant of either pKLFGUS or pKYLXF20GUS. Hence, the FLt promoter with a duplicated enhancer domain is more active than the Flt promoter with a single enhancer domain.

EXAMPLE 3
Expression levels in seedlings (R1 progeny) and young tobacco or Datura plants In order to examine the promoter activity in various tissues during seedling development, the expression of the GUS reporter gene in seedlings (R1 progeny) transformed with pKYLXF20-GUS, or pKLF2-GUS was examined by fluorometric assay of tissue extracts and by histochemical staining of transverse sections of leaves, stems and roots. The FMV promoter activity was monitored in 14 day old seedlings grown aseptically on an MS-agar medium in the presence of kanamycin (300 μg/ml) and 3% sucrose. Several independent lines for each construct were studied. Comparison of activities of the FLt promoter indicated a gradient of expression in the following order; the highest level of activity was found in roots followed by leaves and stems. Stable transformants with a double enhancer gave about 5 fold more GUS activity in roots than those with a single enhancer domain.

The histochemical staining shown in FIG. 9 is representative of the staining patterns analyzed in plants expressing high levels of GUS activity. In seedlings and sections of young leaves stained for GUS, the intensity of staining was markedly greater in vascular tissues of young leaves, petioles, stems and roots. The intensity of GUS staining observed in vascular tissue was in the following order: roots>leaves>stems (FIG. 9). The histochemical GUS assay in leaves showed more activity in midribs, veins and other vascular tissue, and in trichomes than in leaf mesophyll and palisade cells. No GUS activity was detected in transgenic plants containing the construct #111-CAT gene (FIG. 9A).

EXAMPLE 4

Expression of the FMV FLt promoter in various flower organs

Figure 10:
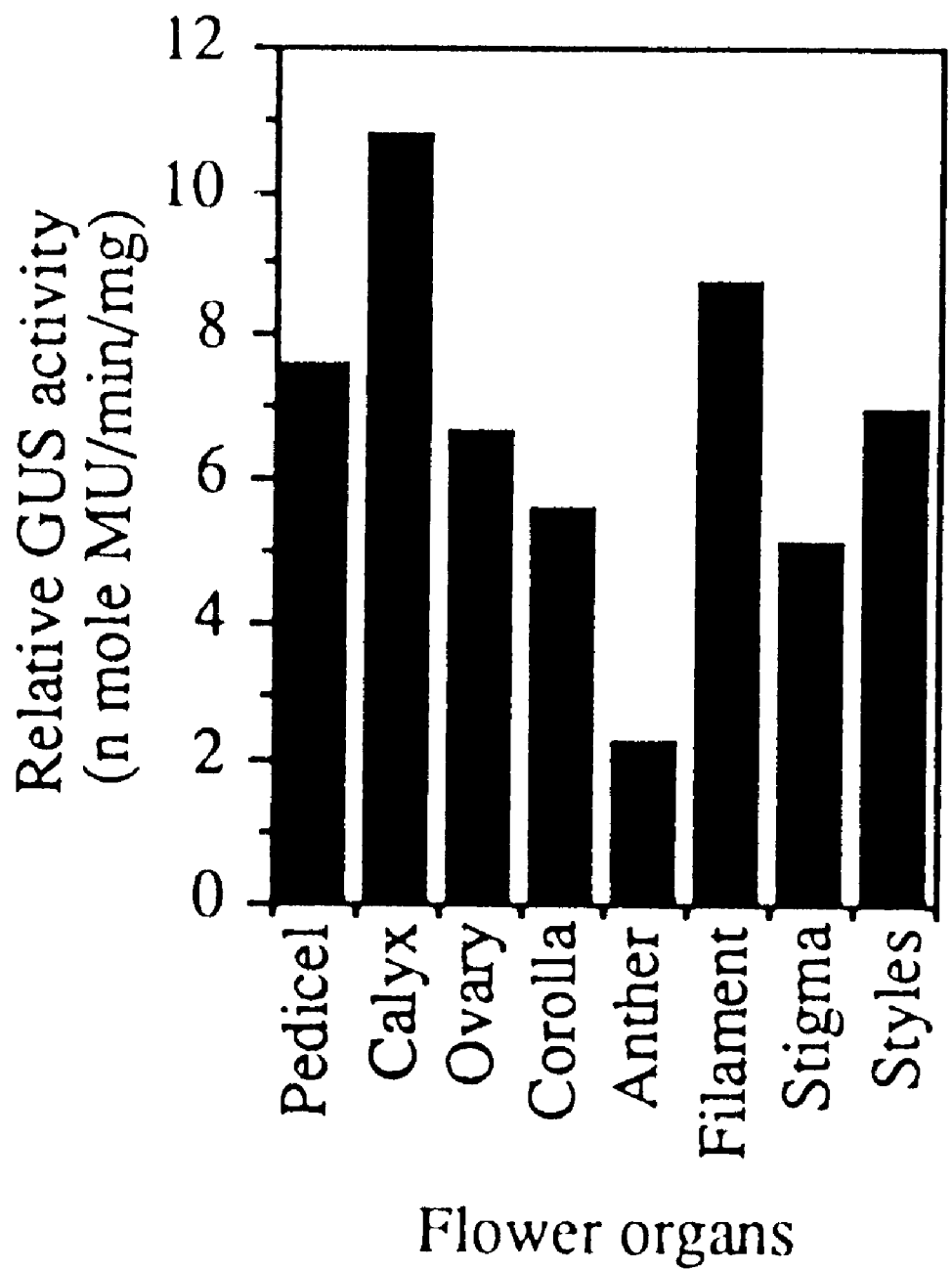
FIG. 10. FMV FLt promoter activity in different flower organs.

FLt promoter activity was examined in flowers from several independent primary lines of construct #110-GUS. Flower samples were collected one day before anthesis. A representative of this analysis with line #7 is shown in FIG. 10. In flowers the highest expression occurred in the calyx, followed by the filament, pedicel, styles, ovary, corolla and stigma. Expression was lowest in anthers. The activity in flowers is relatively low compared to leaves, stems or roots of plants. Similar observations have been made with the CaMV 35S promoter in transgenic tobacco (An et al., 1988).

The disarmed Agrobacterium strain transformed with plant expression vectors containing chimeric gene of interest can be used to engineer desired plants including but not limited to cotton, soybean, alfalfa, oilseed rape, flax, tomoto, sugar beet, sunflower, potato, tobacco, maize, wheat, rice and lettuce, banana, etc. The use of DNA fragment or vectors including FMV promoter sequence tailored with heterologous DNA sequence in the transformation of plants by electroporation or particle gun transformation is within the scope of this invention. These embodiments and examples are provided in order to evaluate the practice of present invention. These examples serve mainly the illustrative purpose, and are not intended to limit the scope of the invention.

TABLE 1

| Constructs | Relative GUS activity (%) |
|---|---|
| Control (TE buffer) | 00 |
| pUC8 GUS (No promoter) | 00 |
| pc-GUS (extra ATG) | 7 |
| pGG1 (CaMV35S) | 35 |
| pFMV 20-GUS (FMV FLt) | 100 |
| pKLF (FMV FLt modified) | 100 |
| pKLF 2 (2 X Enh FMV FLt) | 410 |

Relative β-glucuronidase (GUS) activity of GUS fusion constructs containing different promoters electroporated into tobacco protoplasts. The GUS assay was carried out 20 hrs after electroporation. Assays and conditions were as described in the Methods. Promoter strength is presented as percentage of GUS activity normalized to pFMV 20 GUS for pUC based constructs or pKLFGUS for pKYLX7 based constructs, and represent the mean of three samples from at least two independent experiments,variation was within 12% of the presented value.

The inventors have found that the FLt promoter is a strong, constitutive promoter able to direct gene expression at a level comparable to or exceeding that of the 35S promoter of CaMV. There are extensive similarities in the cis-elements of the 35S and FLt promoters. Both the 35S and FLt promoters contain a consensus TATA-box element (TATATAA) at positions −30 to −24 and −44 to −38 respectively, from the transcription start site. The weaker 19S promoter of CaMV (Guilley et al., 1982) and the FLt promoter of FMV strain M3 (Sanger et al., 1990) carry a non-consensus sequence (TATTTAA) for the TATA-box element. There are three CCAAT-like boxes in the FMV FLt promoter: CCACT (−97 to −93), CACTAA (−92 to −87) and CCACA (−62 to −57); likewise in the 35S promoter these are: CCACT (−85 to −81), CACAAT (−64 to −59) and CCACT (−57 to −53) (Fang et al., 1989; Ow et al., 1987). In the FLt promoter the influence of the CCAAT-element was not evaluated. However this element has been analyzed for other promoters. The deletion of the 5'-most CCAAT-element drastically reduced the activity of the 35S promoter (Ow et al., 1987). In animal systems the importance of the CAAT box has been demonstrated (Bienz et al., 1986). However in the rbcSE9 gene deletion of a putative CAAT-box that showed no negative effect on promoter activity (Morelli et al., 1985).

The region −80 to −63 of the FLt promoter contains the as-1 motif TGACGA repeat (Table 2), that is similar in sequence to that of the 35S promoter 'as-1' element (Lam 1994) at position −82 to −62. The nuclear protein factor ASF-1, mostly responsible for root specific expression, binds within this region, as demonstrated for the 35S promoter (Lam 1994). The as-1 element is important for high expression of promoter activity in young seedlings and leaves by interacting with other adjacent cis-acting units. The leaf-specific element 'as-2', GAT(A/C) repeat sequence of the 35S promoter, at position −105 to −85, interacts with the nuclear factor ASF-2 (Lam et al., 1989). In the 35S promoter, the 'as-2' motif is located 2 bp upstream of the 'as-1' motif. However, in the FLt promoter the 'as-2' like domain GAT(A/T), at position −163 to −151, is located 70 bp upstream of the 'as-1' domain. The as-2 motif has also been identified in similar positions compared to the CaMV 35S promoter in 12 different Cab (chlorophyll a/b binding protein) genes (Lam and Chua 1989).

Besides the CAAT and TATA boxes and the 'as-1' and 'as-2' domains, there are several repeat elements present in both the 35S and FLt promoter sequences which resemble the SV40 core enhancer sequence GTGG/C (Khoury and Gruss 1983). The sequences GTGGGGA (−138 to −132), GTGGGGA (−240 to −234) and GTGGGCA (−286 to −280) in the FLt promoter (Table 2 and FIG. 1) resemble the GTGGAAAAAG (SEQ ID NO:1), GTGGAAAAG (−261 to −253) and GGTAATATC (−325 to −316) sequences of the 35S promoter (Fang et al., 1989). In the FLt promoter, the sequences AAAGA (−116 to −112), AAAGA (−165 to −162), AAAAGGA (−189 to −183), AAAAGCA (−225 to −119) have similarity with AAAGC (−111 to −107), AAAGA (−136 to −132), AAGATGG (−173 to −167) and AAGATGC (−200 to −194) sequences in the 35S promoter. The 5' deletion analysis of the FLt promoter showed that the heptamer sequence repeat, GTGGGGA at position −138 to −132, and at −240 to −234, seems to be important for FLt promoter activity. Further studies will be necessary to evaluate the impact of these upstream repeat sequences on promoter function.

The FMV FLt promoter with longer upstream sequence (−456 to +64) gives less expression compared to the fragment −249 to +64. (See FIG. 11 and section: FMV FLt promoter structure and deletion analysis, page 29 herein.) This result is in contrast to the 35S promoter where a fragment (−1600 to +1) with a longer upstream sequence retained almost full activity compared to a promoter construct extending from −134 to +1 (Ow et al., 1987). It was reported that a promoter sequence isolated from FMV strain M3 exhibited more activity when it contained longer upstream regions (Sanger et al., 1990).

Figure 11A:
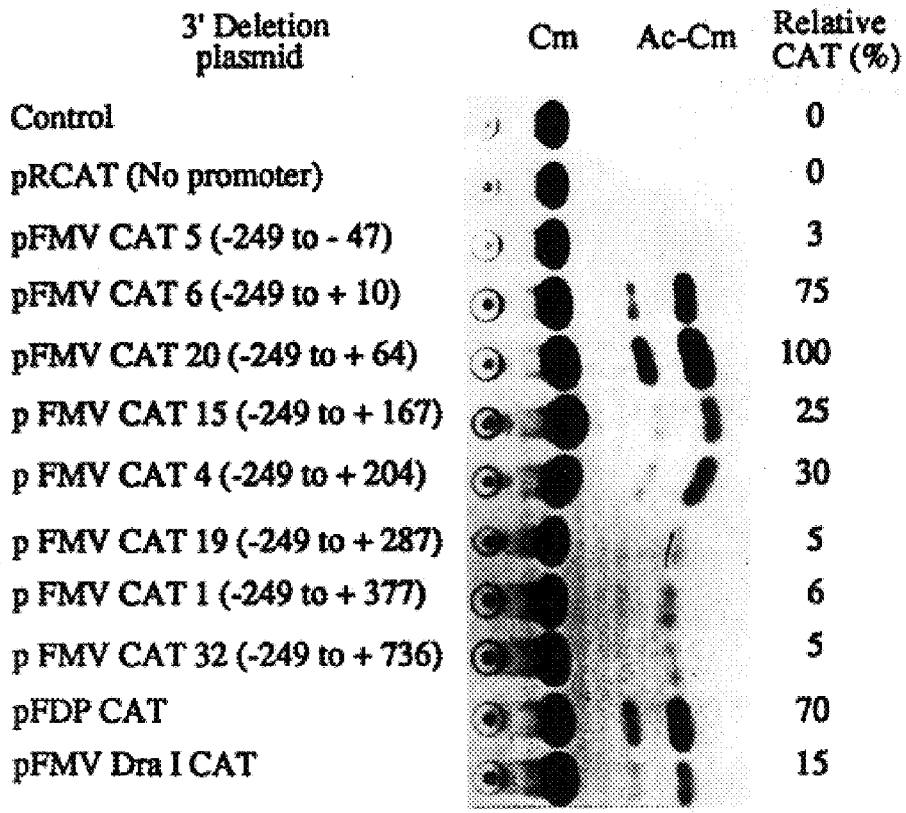
FIGS. 11A and 11B. A deletion analysis of the FMV FLt promoter.
Figure 11B:
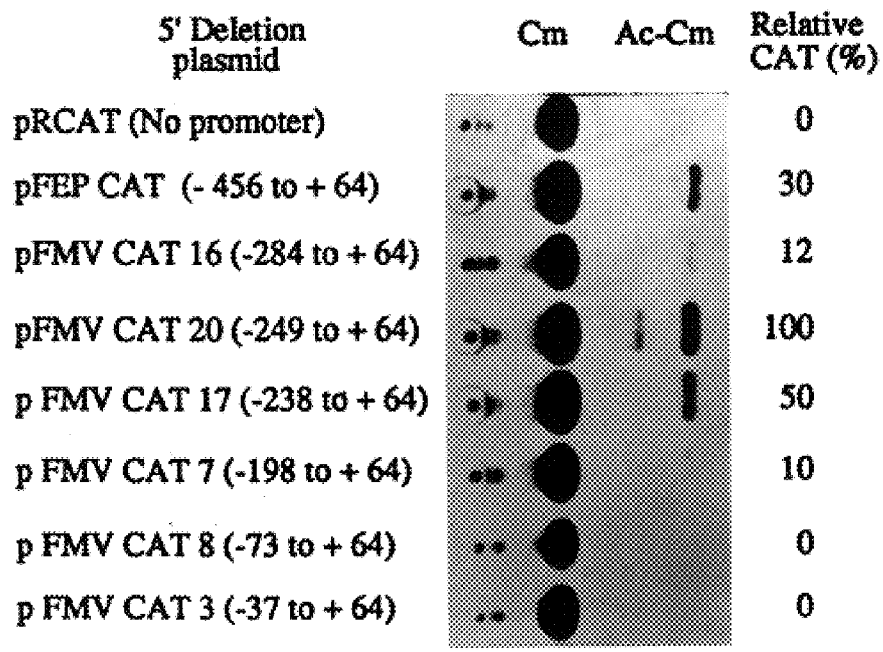

The 3'- and 5'-end deletion analysis of the FLt promoter/leader, studied in transient expression experiments in protoplasts, indicates that a promoter fragment of 313 bp extending from position −249 to +64 with respect to the transcription start site, gives maximum promoter activity. The FLt promoter gives better activity with the longer 3' leader sequence extending to +64 compared to +10 (FIG. 11). Untranslated plant viral leader sequences stimulate expression of a downstream reporter gene (Day Dowson et al., 1993). The 3' leader of the FLt promoter may have some sequence important for initiation of transcription or translation and transcript analysis will be needed to evaluate this putative effect.

Full activity may be due to the location and spacing of the enhancer motifs, specifically the 'as-2' motif in FMV which is apart from the 'as-1' motif, whereas in the 35S promoter both the 'as-1' and 'as-2' motifs are closely associated. In addition, the GTGGGGA repeat elements at position (−138 to −132) and (−240 to −234), separated by 94 nt, seem to be essential for full promoter expression. pFMV CAT 17 (−238 to +64) contains most of the repeat sequences, including one of the GTGGGGA sequences at (−138 to 132) and part of a second upstream GTGGGGA sequence at (−240 to −234). When part of these upstream elements is missing only 50% of full promoter expression is obtained. In pFMV CAT 20 (−249 to +64), inclusion of 11 nt upstream of −238 gives maximum promoter expression, suggesting the importance of the GTGGGGCA sequence. The sequence −249 to −47 upstream of the TATA box contains elements necessary for maximal promoter expression.

When tested with GUS reporter genes in protoplasts, the FLt promoter showed about 2.5-fold more GUS activity compared to the 35S promoter (see Table 1 in Example 1). The sequence from −256 to −55 was duplicated to develop an FLt promoter with a double enhancer domain. This was inserted into the plant expression vector pKLF2. Tandem duplication of enhancer elements of the FLt promoter in pKLF2-GUS or pKLF2-CAT increased gene expression approximately 4–6 fold in transgenic plants. These vectors may be useful for both direct uptake by protoplasts and Ti plasmid-mediated gene transfer.

The expression of useful foreign traits in plants is a major focus in plant biotechnology. For metabolic engineering, where multiple genes need to be inserted into a single cell during the course of transformation, the use of different strong constitutive promoters will be desirable in order to avoid genetic instability caused by recombination between identical promoter sequences.

EXAMPLE 5
Stable transformation and analysis of transgenic plants

The reporter genes CAT or GUS were tailored by PCR to include just the coding sequence with the initiation and termination codons of each gene, flanked by a Xho I site at the 5' end and a Sst I site at the 3' end.

Methods for this example are similar to those set forth in Example 2 above. These were introduced into plant expression vectors. The PCR isolated fragment for the reporter gene (CAT or GUS) was digested with Xho I and Sst I, gel purified and cloned into the corresponding sites of plant expression vectors pKLF or pKLF2. The resulting constructs #109-CAT, 110-GUS, 111-CAT and 112-GUS were introduced into *Agrobacterium tumefaciens* strain C58C1:pGV3850 by triparental mating and tobacco (cv. Samsun NN) was transformed with the engineered Agrobacterium as described earlier (Maiti et al., 1993). The construct #102 in pKYLXF20GUS contains an Eco RI to Hin dIII fragment from pF20GUS cloned into the Eco RI/Hin dIII sites of pKYLX7 by replacing the CaMV 35S promoter flanked by Eco RI and Hind III sites.

To examine the integration of genes in transgenic plants, genomic DNA was isolated following the procedure of Thomson and Henry (1993) for PCR analysis. The integration of the reporter CAT or GUS genes in the genome of transgenic plants (R0 and R1 progeny) was detected by PCR amplification using appropriately designed oligonucleotides specific for the CAT or GUS gene sequence. Specificity of each PCR product was tested by Southern hybridization with a GUS or CAT probe.

EXAMPLE 6
Transient expression experiments, protoplast isolation, and electroporation Isolation of protoplasts from *Nicotiana edwardsonii* cell suspension cultures and electroporation of protoplasts with supercoiled plasmid DNA containing CAT or GUS has been described (Gowda et al., 1989; Kiernan et al., 1993). (Methods are similar to those described in detail in Examples 1 and 2). In brief, an aliquot containing $2 \times 10^6$ protoplasts was electroporated with 50 µg of plasmid DNA. After 20 hr, $2 \times 10^5$ protoplasts were harvested for each CAT or GUS assay.

EXAMPLE 7
Chloramphenicol acetyl transferase (CAT) and β-glucuronidase (GUS) assays CAT activity was determined according to the published method (Gorman et al., 1982). Plant tissue extracts containing 5 µg of soluble protein were used for each CAT assay. The reaction was carried out at 37° C. for 30 min. The rates of reaction were linear over the period of incubation. Fluorometric GUS assays to measure GUS activity of plant tissue extracts and histochemical GUS assays to determine the distribution of GUS activity in plants (embryos and seedlings), were performed according to published procedures (Jefferson et al., 1987). Protein in plant extracts was estimated (Bradford 1976) using BSA as a standard. For the fluorometric assays, samples were homogenized in GUS extraction buffer (50 mM NaPO4, pH 7.0, 10 mM β-mercaptoethanol, 10 mM Na2 EDTA, 0.1% Na Sarkosyl, 0.1% Triton X-100), and centrifuged for 10 min at full speed in a microcentrifuge. Soluble protein (5 µg) from transgenic plant tissue extracts were incubated with 4-methyl umbelliferyl glucuronide (MUG) solution for 10 to 20 min, after which fluorescence was measured. Fluorescence of a solution of 100 p mol 4-methyl umbelliferone (MU) in 0.2 M sodium carbonate was used for calibration. Fluorescence was measured on a minifluorometer (Model No TKO 100: Hoefer, San Francisco, Calif.), with an excitation wavelength of 365 nm and photodetector wavelength of 460 nm.

For histochemical staining to detect GUS activity, seedlings or plant tissue sections were placed in GUS histochemical buffer (100 mM NaPO 4, 0.5 mM K3[Fe(CN)6], 0.5 mM K4[Fe(CN)6], 10 mM EDTA, 1 mg/ml 5-bromo-4 chloro-3-indolyl-β-D-glucuronide (X-gluc) in vacuo for 10 min, followed by incubation at 37° C. for 1 to 18 hr. Samples were evaluated for the rate and intensity of color development in tissues.

EXAMPLE 8
Structure of the FMV FLt promoter and analysis of deletion constructs In order to define the regions of the FLt promoter needed for maximal expression, a 3'- and 5'-end deletion analysis was carried out on the appropriate DNA fragment from the FMV genome (Richins et al., 1987) (genome coordinates 6481 to 7680). The start site of transcription (ACTGAA, start site in bold letter, coordinate 6939 of the FMV genome) to produce the full length transcript (Scholthof et al., 1992) was determined by primer extention analysis (data not shown). The FLt promoter contains a consensus TATA box (TATATAA) at position −44 to −38, a CAAT box like sequence (CCACT) at position −97 to −93, an as-1 enhancer elements (TGACG), an as-2 motif and several repeat sequences resembling the SV40 core element GTGG/C sequence (Khoury and Gruss 1983) (Table 2).

TABLE 2

A list of DNA repeat sequences and other putative regulatory elements in the FMV FLt promoter, (FMV coordinates 6481 to 7680, of 1200 bp fragment)

| Designation of sequence | Repeat sequence or regulatory elements | Position | Spacing (nt) between successive domains |
|---|---|---|---|
| 1a | TGACGA | −68 to −63, | 6 |
| 1b | TGACGA | −80 to −75 | |
| (as-1 motif) | | | |
| 2a | AAAGA | −116 to −112 | 44 |
| 2b | AAAGA | −165 to −162 | |
| 3a | GTGGGGA | −138 to −132 | 94 |
| 3b | GTGGGGA | −240 to −234 | 40 |
| 3c | GTGGGCA | −286 to −280 | |
| 4a | GATT | −163 to −160 | 4 |
| 4b | GATA | −154 to −151 | |
| (as-2 like) | | | |
| 5a | AAAAGGA | −189 to −183 | 29 |
| 5b | AAAAGCA | −225 to −119 | |
| 6a | GGCGCA | −201 to −196 | 9 |
| 6b | GGTGCA | −216 to −211 | |
| 7a | AAAGTAA | −277 to −273 | 13 |
| 7b | AAAGTTA | −293 to −287 | 26 |
| 7c | TAAGTTT | −326 to −320 | |
| 8a | AAGAC | −300 to −296 | 8 |
| 8b | AAGAC | −313 to −309 | |
| 9a | TCCAAAGC | −447 to −440 | 25 |
| 9b | TCCAAACC | −414 to −406 | 5 |
| 9c | GCCAAAAGC | −402 to −394 | |
| 10a | TCAA | −438 to −435 | 50 |
| 10b | TCAA | −384 to −380 | 10 |
| 10c | TCAA | −370 to −367 | 0 |
| 10d | TCAA | −366 to −363 | |
| 11a | ATCAAAGTA | −385 to −377 | 9 |
| 11b | ATCAATGAA | −367 to −359 | |
| CAAT-box | CCACT | −91 to −93 | |
| TATA-box | TATATAA | −44 to −38 | |
| polyA track | AATAAA | +125 to +130 | |
| TATA like | TATAAAATA | +180 to +188 | |

The FMV FLt promoter was subcloned into pUC 119 from the FMV strain DxS genome (Richins et al., 1987). In order to define the 3' boundary of the promoter/leader for maximum expression of the reporter gene, a set of nested 3' deletion plasmids with the 5' end point at −249 were selected for analysis. These constructs were introduced into tobacco protoplasts by electroporation for transient expression assays. The construct pFMV CAT20 (−249 to +64), (Gowda et al., 1989) showed maximum expression, and for comparison with other constructs this value was considered to represent 100% of full activity. The constructs pFMV CAT 32, pFMV CAT 1 or pFMV CAT 19, with 3' ends at +736, +377 or +287 respectively, gave much lower CAT activity than pFMV CAT20. Further deletion to +204 or +167 increased the promoter expression to 25–30% of full activity. However, this was still significanly lower than the activity of the plasmid pFMV CAT 20 (−249 to +64), which showed the maximum expression.

These results show that the leader sequence from +167 to +736 has a significant inhibitory effect on expression activity, probably through its effect on translation of the transcript. This depressing effect of the leader sequence on expression has been documented earlier for both FMV (Gowda et al., 1989) and CaMV (Baughman and Howell 1988). The 3' deletion to +10 in pFMV CAT 6 showed about 75% maximal promoter expression compared to pFMV CAT 20. This suggests that for better expression a longer 3' leader is necessary for the FLt promoter. FMV FLt promoter expression was significantly reduced by deleting the sequence to −47 in pFMV CAT 5 (TATA box region) from the 3' end, demonstrating the importance of a TATA box sequence in the FMV FLt promoter.

In the downstream sequence of the FMV FLt promoter, there is a TATA like sequence (TATAAAATA) at position +180 to +188 after the poly A signal (AATAAA) at position +125 to +130 (Table 2). An internal deletion mutant pFD-PCAT was generated from pFMV 19 (−249 to +287) by deleting a 199 bp segment (−53 to +144) containing the TATA box at position −44 to −38 and the poly A track at position +125 to +130. Interestingly, this promoter/leader mutant pFDP CAT showed expression of about 70% of full activity, suggesting that the TATAAAATA sequence may substitute for the upstream normal TATA -box in this context.

The mutation of the poly A signal AATAAA to the sequence TTTAAA in pFMV Dra I CAT derived from pFMV CAT 15 (−249 to +167) resulted in about 40% less activity compared to pFMVCAT15, indicating some importance of this sequence for proper expression in this context. However, from 3' deletion analysis, the 313 bp promoter fragment (−249 to +64) in pFMV CAT 20 was found to be sufficient for high expression of the reporter gene. Therefore, for 5' deletion analysis, the 3' end point was fixed at +64.

EXAMPLE 9
The effect of 5' deletion on FMV FLt promoter function was evaluated by transient expression in protoplasts A series of 5' deletion constructs with their 3' end at +64 with respect to the transcription start site were generated. The 5' deletion plasmid pFMV CAT 3, (−37 to +64) without a TATA box sequence, or pFMV CAT 8, (−73 to +64) with a TATA box sequence and part of an 'as-1' domain, showed no expression, suggesting dependency on additional upstream sequence elements. A similar effect has also been documented for the CaMV 35S promoter. The 5' deletion construct pFMV CAT 7, consisting of a fragment with sequence −198 to +64 from the start site containing the TATA box, the 'as-1' domain and the CCACT sequence, showed very little activity (10% of full activity), suggesting that further upstream elements are needed for promoter expression. In pFMV CAT 17 (−238 to +64), the level of expression is about 50% of the full activity shown by pFMV CAT 20 (−249 to +64). This suggests that sequence elements between −198 and −249 probably comprise a domain necessary in addition to downstream elements for maximal promoter expression. Interestingly, inclusion of the upstream sequence beyond −249 in the mutant pFMV CAT 16 (−284 to +64) reduced the promoter expression to 12% of full activity.

The construct pFEP CAT (−456 to +64) with a longer upstream segment dropped about 30% in its expression compared to the pFMV CAT 20. The sequence between −249 and −284 may have a negative regulatory effect. On the basis of deletion analysis with the FLt promoter, the fragment −249 to +64 seems to be composed of cis-elements necessary for strong promoter activity. Consequently, this promoter fragment was tested for expression activity in transgenic plants.

Examples Heterologous Genes which may be used with FMV FLt Promoter

Plant genetic engineering techniques allow researchers to introduce heterologous genes of interest into plant cells to obtain the desired qualities. A strong constitutive promoter like FMV FLt promoter is useful to direct the any gene to be used for plant genetic engineering, a field of biotechnology which is leading a rapid progress in the production of economically valuable germplasm with improved characters or traits such as:

1. Insect resistance, (developed with Bt toxin gene, α-amylase inhibitor gene).
2. Virus resistance, (developed with CP, protease or replicase gene).
3. Fungal resistance, (developed with chitinase gene, ribosome inhibiting protein gene, glucanase gene).
4. Herbicide resistance, (developed with acetolactate synthase, phosphinothricin acetyl transferase or bar gene, nitrilase gene, or 2,4-dichlorophenoxyacetate monooxygenase gene).
5. Bacterial or nematode pathogen resistance, (developed with α-hordothionin gene, Bt toxin gene, beet cyst nematode resistant locus).
6. Cold or drought tolerance.
7. Improved nutritional value, (developed with seed storage protein genes).
8. Seed oil modification, (developed by controlling chain length and saturation with fatty acid synthesis genes including stearoyl-ACP desaturase, oleoyl-ACP thioesterase, β-ketoacyl-ACP synthase and acyl-ACP thioesterase).
9. Delayed ripening of fruits, (developed by controlling ethylene producing genes, ACC oxidase gene).
10. Male sterility.
11. Modification of carbohydrate (developed with antisence gene of granule bound starch synthase, branching enzyme encoding genes, glgB).
12. Protein/peptides controlling human disease (Therapeutic peptides, proteins such as RMP-7, AC137, antithrombin hirudin, growth hormone, interleukin could be produced in plant-based system) to name a few examples.

The above heterologous genes, and other heterologous genes may be inserted into plasmids pKLF and pKLF2 by genetic engineering methods known in the art. These newly created germplasms can enhance breeding programs for crop improvement, as well providing as a better understanding of gene regulation and organization in transgenic plants. Plant metabolic engineering is the application of genetic engineering methods to modify the nature of chemical metabolites in plants. For metabolic engineering where multiple genes need to be inserted into one cell, the use of different, strong, constitutive promoters is desirable in order to avoid genetic instability caused by recombination between identical or closely related promoter sequences taken from plants themselves. Through use of the promoter sequences of the invention the introduced genes can be transcribed to messenger RNA and then RNA translated to resultant proteins that exhibit new traits or characters. The invention described herein, in developing gene vectors with newly defined promoters of the caulimoviruses, advances this effort.

A wide variety of well-characterized genes of animal, human, bacterial and of plant origin, including those of several viruses, are available for engineering plants. For the most effective expression of this wide selection of genes either constitutive or regulated, versatile gene expression vectors are required.

DETAILED DESCRIPTION OF THE FIGURES

FIG. 1 show the DNA sequence of the full length transcript promoter and the 3' leader sequence and the 5' portion of gene VII from the figwort mosaic virus (FMV) strain DxS (Richins et al., 1987). The nucleotide sequence (FMV coordinates 6481 to 7680, a 1200 bp fragment) includes the 3' end of gene VI, part of the large intergenic region, presented in the 5' to 3' direction of the transcript from left to right. The TATA box, CCACT box and poly A signal sequence (AATAA) are shown in bold. The transcription initiation site for the full length FMV transcript is indicated as +1, (position 6939 in the FMV genome). Repeat sequence domains (Ia, Ib to 11a, 11b as indicated, listed in Table 2) are under lined or overlined. These sequence motif may be important for the promoter activity.

FIG. 2 shows construction strategy of FMV FLt promoter with its single and double enhancer domains. Number in parenthesis indicate nucleotide position in the FMV genome.

FIG. 3 shows a physical map of pKYLX71.

Figure 4A:
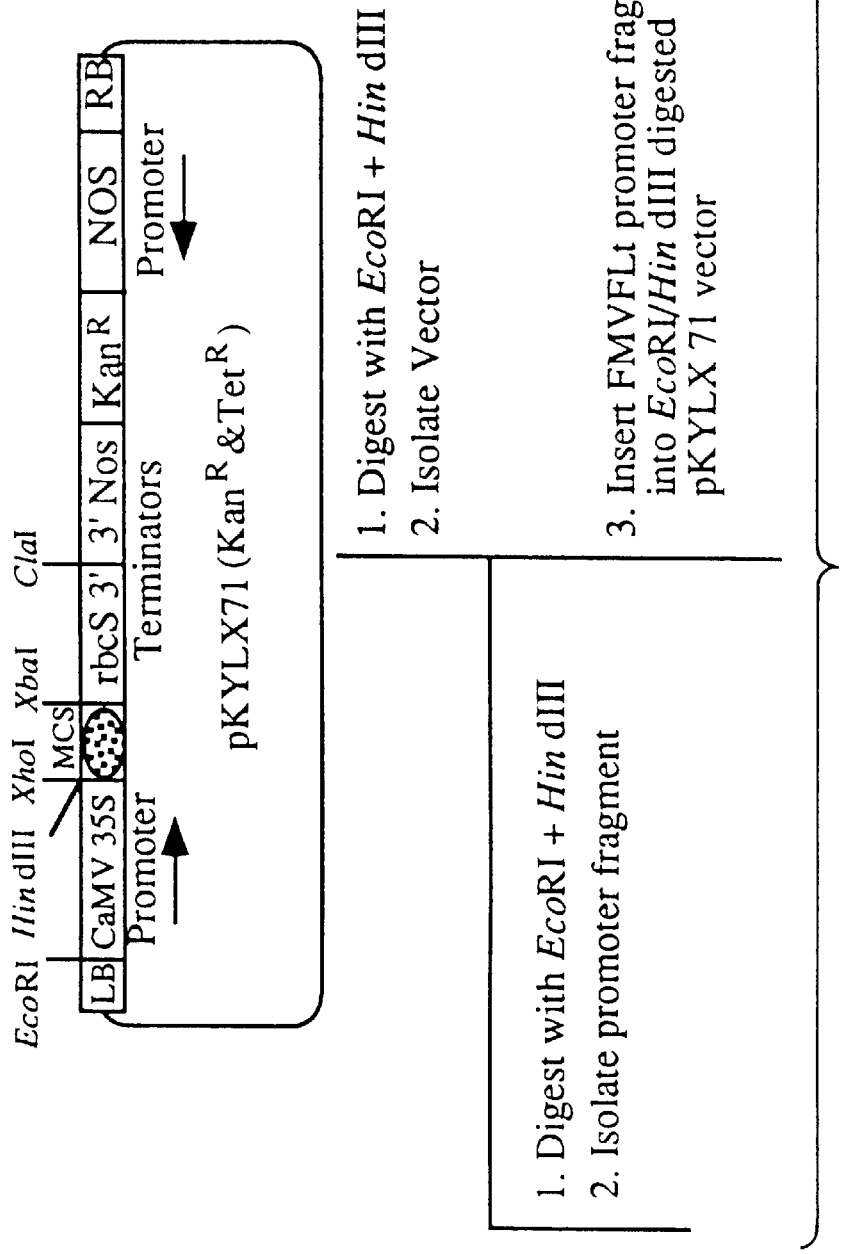

FIG. 4 shows the construction strategy and physical map of pKLF.

FIG. 5 shows the construction strategy and physical map of pKLF2.

FIGS. 6 A and B. show a schematic representation of chimeric GUS or CAT constructs used for assaying promoter activity in transient expression analysis (A) and transgenic plants (B). The identity of the respective promoter is shown for each plasmid. GUS represents the gene for β-gulcuronidase of $E.$ $coli.$, CAT represents bacterial chloramphenicol acetyl transferase gene. The position XhoI (X), SacI (S), BamHI (B), EcoRI (E), HindIII (H), Cla I (C), SphI (Sp) used to assemble these plasmids are given. The position of the left and right T-DNA borders (LB and RB respectively) the rbcS polyadenylation signal (3' REGION) and the Kmr gene are illustrated. NT3' or RT3' represent the polyadenylation sequences from NOS or RbcS gene respectively.

FIG. 7 shows a FMV FLt promoter activity in transgenic plants expressing a CAT reporter gene: Comparison of the modified FMV FLt promoter activity in transgenic plants Nicotiana tabacum cv Samsun NN (R0 progeny) expressing a CAT reporter gene. Promoter activity was analyzed in independent lines developed with construct #109-CAT (A) with a FMV FLt-promoter single enhancer domain or construct #111-CAT (B) with FMV FLt2 promoter containing a duplicated enhancer domain. The plasmids carrying these constructs are pKLF-CAT and pKLF2-CAT respectively. CAT activity was determined in tissue extracts (5 µg of total soluble protein) from fully expanded leaves. Enzyme activity (CAT %) is expressed as percent conversion of chloramphenicol (Cm) to acetylated chloramphenicol (Ac-Cm). Lanes with control untransformed tobacco leaf extract (C) from Samsun NN and transformed control (Tc) with the GUS reporter gene from transgenic tobacco leaf developed with construct #112-GUS.

FIG. 8. shows a comparison of the wild type and modified FMV FLt promoter activity in transgenic *Nicotiana tabacum* cv Samsun NN (R0 progeny) expressing a GUS reporter gene. Relative GUS activity of independent lines #1, 3, 4, 5, 6, 7 from transformation with construct #102-GUS (wild typeFMV FLt promoter with a single enhancer domain-GUS); and independent lines #1, 2, 3, 6, 7, 8, 11, 12, 13 generated for construct #110-GUS (modified FMV FLt promoter and with a single enhancer domain-GUS) independent lines #1, 11, 12, 13, 14, 16, 17, and 18 from transformation with construct #112-GUS (FMV FLt promoter with a double enhancer-GUS). Soluble protein extract (5 μg) from fully expanded leaves of transformed lines were used for the GUS assays.

FIG. 9 shows a histochemical localization of GUS activity in developing transgenic tobacco (A to I) and *Datura inoxia* (J to O) plants containing the GUS reporter gene directed by the FLt promoter.

A. Transgenic tobacco seedling (X10), (pKLF2 CAT #9, R1 progeny) with CAT gene; no GUS activity was detected.

B. Seedling (X10), (pKLF2-GUS#12, R1 progeny) at 10 DAI; GUS activity was localized in the roots, root hairs, leaves, stems and apical meristematic region.

C. Close up view of young leaf (X40) from 10 day old seedling (pKLF2 GUS, R1 progeny); more activity in veins.

D. Mature leaf section (X5) from six week old plants (pKLF2GUS, R1 progeny); more GUS staining in midrib and veins.

E to G. Roots from six week old seedlings (pKLF 2-GUS #12), Longitudinal section of a matured root (X40) stained for 2 hrs (E), prolonged staining for 18 hrs (F), and root tip (G); staining in the root was most intense at the tip (X20), vascular tissue and in root hairs.

H. Transverse stem section (X20) from a seedling (pKLF2GUS #12, R1 progeny) at 14 DAI; GUS activity was localized at vascular (v) and epidermis (e) regions.

I. Trichomes (X25), most intense GUS activity localized at head cells.

J. Transgenic *Datura inoxia* seedlings (X25), (pKYLX20GUS, R1 progeny) at 12 DAI, grown axenically on filter paper. GUS activity is localized primarily in the root (root tip & hairs) and in the lower hypocotyl.

K. and L. Roots (X25) from 4 week old *Datura inoxia* seedlings (pKYLX20GUS, R1 progeny) grown in greenhouse, longitudinal section (K) and cross-section (L); GUS activity was more intense in the vascular tissue.

M to O. Transverse section of petiole (X25), (M); stem (X25), (N); and midrib (X25), (O) from 4 weeks old *Datura inoxia* seedlings (pKYLXF20GUS, R1 progeny) grown in greenhouse. GUS staining was more intense in the vascular system. Legend: a, apical meristem; e, epidermis: h, hypocotyl; v, vascular tissue; r, root; rc, root cap.

FIG. 10 shows FMV FLt promoter activity in different flower organs. Transgenic tobacco flowers were sampled one day before anthesis. GUS activity was measured in extracts from each type of tissue as indicated in figure.

FIG. 11 shows transient expression analysis of 3' and 5' deletion plasmids of the FMV FLt promoter. Downstream deletion end points of each plasmid are indicated in parenthesis. CAT activities are presented as percentage activity of the 3' deletion construct pFMV20CAT. Each construct was assayed at least four times; variation was within 10% of presented value. Cm=chloramphenicol and Ac-Cm=acetylated chloramphenicol.

REFERENCES

An, G., Costa, M. A., Mitra, A., Ha, S-B. and Marton, L. (1988) Organ-specific and developmental regulation of the nopaline synthase promoter in transgenic tobacco plants. Plant Physiol. 88: 547–552.

Benfey, P. N, Ren, L. and Chua N-H (1990a) Tissue-specific expression from CaMV 35S enhancer subdomains in early stages of plant development. EMBO J. 9: 1677–1684.

Benfey, P. N. and Chua, N-H. (1990). The cauliflower mosaic virus 35S promoter: Combinatorial regulation of transcription in plants. Science 250: 959–966.

Benfey, P. N., Ren, L and Chua, N-H. (1990b) Combinatorial and synergistic properties of CaMV 35S enhancer subdomains. EMBO J. 9: 1685–1696.

Benfey, P. N., Ren, L. and Chua, N-H. (1989) The CaMV 35S enhancer contain at least two domains which can confer different developmental and tissue-specific expression patterns. EMBO J. 8: 2195–2202.

Berger, P. H., Hunt, A. G., Domier, L. L., Hellmann, G. M. Stram, Y., Thornbury, D. W. and Pirone, T. P. Expression in transgenic plants of a viral gene product that mediates insect transmission of potyviruses. Proc. Natl, Acad. Sci. (USA) 86: 8402–8406.

Bonneville, J. M. and Hohn, T. (1993) In "Reverse Transcriptase" (A. M. Skalka and S. P. Goff, eds), pp 357–390, Cold Spring Harbor Laboratory Press, Cold Spring Harbor, N.Y.

Bouchez, D., Tokuhisa, J. G., Llewellyn, D. J., Dennis, E. S. and Ellis, J. G. (1989) The ocs-element is a component of the promoters of several T-DNA and plant viral genes. EMBO J. 8: 4197–4204.

Bradford, M. M. (1976) A rapid and sensitive method for the quantitation of microgram quantities of protein utilizing the principle of protein-dye binding. Anal. Biochem. 72: 248–254.

Cooke, R. and Penon, P. (1990). In vitro transcription from cauliflower mosaic virus promoters by a cell-free extract from tobacco cells. Plant Mol. Biol. 14: 391–405.

Covy, S. N. and Hull. R. (1992) Genetic engineering with double-stranded DNA viruses. In: "Genetic engineering with plant viruses" (T. M. A. Wilson and J. W. Davis, eds), pp 217–249. CRC Press, Boca Ratonl, Fla.

Daubert, S., Richins, R. D., Shepherd, R. J., and Gardner, R. C. (1982) Maping of the coat protein gene of cauliflower mosaic virus by its expression in a prokaryotic system. Virology 122: 444–449.

Daubert, S., Shepherd, R. J., and Gardner, R. C. (1983) Insertional mutagenesisof the cauliflower mosaic virus genome. Gene 25: 201–208.

Dixon, L. and Hohn, T. (1984) Initiation of translation of the cauliflower mosaic virus genome from a polycistronic mRNA evidence from deletion mutagenesis. EMBO J. 3: 2731–2736.

Driesen, M., Benito-Moreno, R-M., Hohn, T., and Futterer, J. (1993) Transcription from the CaMV 19S promoter and autocatalysis of translation from CaMV RNA. Virology 195: 203–210.

Ducasse, D. A. Mushegian, A. R. and Shepherd, R. J. 1995. Gene I mutants of peanut chlorotic streak virus, a caulimovirus replicate in planta but do not move from cell to cell. Jour. Virology 69: 5781–5786

Fang, R-X., Nagy, F., Sivasubramanian, S. and Chua, N-H. (1989) Multiple cis regulatory elements for maximal expression of the cauliflower mosaic virus 35S promoter in transgenic plants. Plant Cell 1: 141–150.

Fromental, C., Kanno, M., Nomiyama, H. and Chambon, P. (1988) Cooperativity and hierarchical levels of functional organization in the SV 40 enhancer. Cell 54: 943–953.

Gardner, R. C., Howarth, A. J., Hahn, P., Brown-Leudi, M. and Shepherd, R. J (1981) The complete nucleotide sequence of an infectious clone of cauliflower mosaic virus by M13mp7 shortgun sequencing. Nucleic Acids Res. 9: 2871–2888.

Giband, M., Mesnard, J-M., and Lebeurier, G. (1986). The gene III product (P15) of cauliflower mosaic virus is a DNA-binding protein while an immunologically related P11 polypeptide is associated with virions. EMBO J. 5: 2433–2438.

Gordon, K., Pfeiffer, P., Futterer, J. and Hohn, T. (1988) In vitro expression of cauliflower mosaic virus genes. EMBO J. 7: 309–317.

Gorman, C. M., Moffat, L. F. and Howard, B. H. (1982) Recombinant genomes which express chloramphenicol acetyltransferase in mammalian cells. Mol. Cell Biol. 2: 1044–1051.

Gowda, S., Scholthof, H. B., Wu, F. C. and Shepherd, R. J. (1991) Requirement of gene VII in cis for the expression of downstream genes on the major transcript of figwort mosaic virus. Virology 185: 867–871.

Gowda, S., Wu, F. C., Herman, H. B. and Shepherd, R. J. (1989) Gene VI of figwort mosaic virus (caulimovirus group) functions in posttranscriptional expression of genes on the full-length RNA transcript. Proc. Natl. Acad. Sci. USA 86: 9203–9207.

Graybosh, R., Hellmann, G. M., Shaw, J. G., Rhoads, R. E. and Hunt, A. G. 1989. Expression of a potyvirus non-structural protein in transgenic tobacco. Biochem. Biophys. Res. Commun. 160: 425–432.

Hasegawa, A., Verver, J., Shimada, A., Saito, M., Goldbach, R., van Kammen, A., Miki, K., Kameya-Iwaki, M. and Hibi, T. (1989) The complete sequence of soybean chlorotic mottle virus DNA and the identification of a novel promoter. Nucl. Acids Res.17: 9993–10013.

Howell, S. H. and Hull, R. (1978) Replication of cauliflower mosaic virus and transcription of its genome in turnip leaf protoplasts. Virology 86: 468–481.

Hull, R., Sadler, J. and Longstaff, M. (1986) The sequence of carnation etched ring viral DNA: comparison with cauliflower mosaic virus and retroviruses. EMBO J. 5: 3083–3090.

Jefferson, R. A., Kavanagh, T. A. and Bevan, M. W. (1987) GUS fusion: β-Glucuronidase as a sensitive and versatile gene fusion marker in higher plants. EMBO J. 6: 3901–3907.

Kay, R., Chan, R., Daly, M. and McPherson, J. (1987) Duplication of CaMV 35S promoter sequence creats a strong enhancer for plant genes. Science 236: 1299–1302.

Kiernan, J. M., Wu, F. C., Goldberg, K-B., Gowda, S. and Shepherd, R. J. (1993) Transformation in *Nicotiana edwardsonii*, In: Biotechnology in Agriculture and Forestry, Vol 22, Plant Protoplasts and Genetic Engineering III, (Ed Y. P. S. Bajaj), Springer-Verlag Berlin Heidelberg.

Lam, E. (1994) Analysis of tissue-specific elements in the CaMV 35S promoter. In: Results and Problems in Cell differentiation, Vol 20, pp 181–196, L. Nover (ed, Plant Promoters and transcription factors, Springer-Verlag Berlin Heidelberg.

Lam, E., Benfey, P. N., Gilmartin, P. M., Fang, R-X. and Chua, N-H. (1989) Site-specific mutation alter in vitro factor binding and change promoter expression pattern in transgenic plants. Proc. Natl. Acad. Sci. USA 86: 7890–7894.

Lam, E. and Chua, N-H. (1989) GT-1 binding site confers light responsive expression in transgenic tobacco. Science 248: 471–474

Liod, A. M., Walbot, V., Davis, R. W. (1992) Arabidopsis and Nicotiana anthrocyanin production activated by maize regulators R and Cl. Science 258: 1773–1775.

Maiti, I. B. Von Lanken , C.,and Hunt, A. G. 1995 Properties of transgenic plants that express a functional potyvirus P1 proteinase gene. Manuscript submitted Maiti, I. B., and Hunt, A. H. 1992. Expression of the tobacco vein mottling virus nuclesr inclusion protein (NIa) gene in tobacco. J. Cell. Biochem. Supplement 16F, Abs#Y213.

Maiti, I. B., Hunt, A. G., and Wagner, G. J. 1988. Seed-transmissible expression of mammalian metallothionein in transgenic tobacco. Biochem. Biophys. Res. Commun. 150: 640–647.

Maiti, I. B., Hong, Y., Hellman, G. M., Lanken, C. V. and Hunt, A. 1994. Multiple potyvirus genes do not confer protection upon plants additively. In 4th congress of ISPMB meeting, Jun. 19–24, 1994. Amsterdam, The Netherlands, (abstract).

Maiti, I. B., Murphy, J., Shaw, J. G., and Hunt, A. H. (1991) Expression of the tobacco vein mottling virus coat protein (CP) and cylinderical inclusion protein (CI) genes in tobacco. In 3rd Int. Congress Int. Soc. Plant Mol. Biol. p 1154.

Maiti, I. B., Murphy, J. F., Shaw, J. G., and Hunt, A. G. (1993) Plants that express a potyvirus Vpg-proteinase gene are resistance to virus infection. Proc. Natl. Acad. Sci. (USA) 90: 6110–6114.

Maiti, I. B., Wagner, G. J. and Hunt A. G. (1991) Light inducible and tissue-specific expression of a chimeric mouse metallothionein cDNA gene in tobacco. Plant Science 76: 99–107.

Maiti, I. B., Wagner, G. J., Yeargan, R., and Hunt, A. G. (1989) Inheritance and expression of the mouse metallothionein gene in tobacco. Plant Physiol. 91: 1021–1024.

Maiti, I. B. and Hunt, A. G. (1992) Developing genetically engineered disease, pest and herbicide resistance in tobacco. Rec. Adv. Tobacco Sci. 18: 45–68.

McNeall, J., Sandey, A. Gray, P. P. Chesterman, C. N. and Sleigh, M. J. 1989. Hyperinducible gene expression from a metallothionein promoter containing addetional metal responsive elements. Gene 76: 81–88.

Odell, J. T., Nagy, F. and Chua, N-H. (1985) Identification of DNA sequence required for activity of the cauliflower mosaic virus 35S promoter. Nature 313: 810–812.

Odell, J. T. and Howell, S. H. (1980) The identification, mapping and characterization of mRNA for p66, a cauliflower mosaic virus-encoded protein. Virology 102: 349–359.

Odell, J. T., Dudley, R. K. and Howell, S. H. (1981) Structure of the 19S RNA transcripts encoded by the cauliflower mosaic virus genome. Virology 111: 377–385.

Odell, J. T., Knowlton, S., Lin, W, and Mauvais, C. J. (1988) Properties of an isolated transcription stimulating sequence derived from the cauliflower mosaic virus 35S promoter. Plant Mol. Biol. 10: 263–272.

Omirulleh, S., Abraham, M., Golovkin, M., Stefanov, I., Karabaev, M. K., Mustardy, L., Morocz, S. and Dudits, D. (1993) Activity of a chimeric promoter with the double CaMV 35S enhancer elements in protoplast-derived cells and transgenic plants in maize. Plant Mol. Biol. 21: 415–428.

Ondek, B., Gloss, L. and Herr, W. (1988) The SV 40 enhancer contains two distinct levels of organization. Nature 333, 40–45.

Ow, D. W., Jacobs, J. D. and Howell, S. H. (1987) Functional region of the cauliflower mosaic virus 35S RNA promoter determined by the use of the firefly luciferase gene as a reporter of promoter activity. Proc. Natl. Acad. Sci. USA 84: 4870–4874.

Prat, S., Willmitzer, L. and Sanchez-Serrano, J. J. 1989. Nuclear protein binding to a cauliflower mosaic virus 35S truncated promoter. Mol. Gen. Genet. 217: 209–214.

Reddy, D. V. R., Richins, R. D., Rajeshwari, R., Iizuka, N., Manohar, S. K. and Shepherd, R. J. (1993) Peanut chlorotic streak virus, a new caulimovirus infecting peanuts (Arachis hypogaea) in India. Phytopathology 83: 119–133.

Richins, R. D. (1993) Organization and expression of the peanut chlorotic streak virus genome. Ph. D. Dissertation, at the University of Kentucky, Lexington, Ky., USA.

Richins, R. D., Broos, T., Ducasse, D. A., Gowda, S., Mushegian, A. R., Reddy, D. V. R. and Shepherd, R. J. (1995) organization and transcription of the peanut chlorotic streak virus genome. Mol. Plant Microbe Interact. (in press).

Richins, R. D., Scholthof, H. B. and Shepherd, R. J. (1987) Sequence of figwort mosaic virus DNA (caulimovirus group). Nucleic Acids Res. 15: 8451–8466.

Sanger, M., Daubert, S. and Goodman, R. M. (1990) Characteristics of a strong promoter from figwort mosaic virus: comparison with the analogous 35S promoter from cauliflower mosaic virus and the regulated mannopine synthase promoter. Plant Mol. Biol. 14: 433–443.

Schardl, C. L., Byrd, A. D., Benzion, G., Altschuler, M. A., Hildebrand, D. F. and Hunt, A. G. (1987) Design and construction of a versatile system for the expression of foreign genes in plants. Gene 61: 1–11.

Schirm, S., Jiricny, J. and Schaffner, W. (1987) The SV40 enhancer can be dissected into multiple segments, each with a different cell type specificity. Genes. Dev. 1: 65–74.

Scholthof, H. B., Gowda, S., Wu, F. and Shepherd, R. J. (1992) The full-length transcript of a caulimovirus is a polycistronic mRNA whose genes are transactivated by the product of gene VI. J. Virol. 66: 3131–3139.

Shepherd, R. J., Richins, R. D., Duffus, J. E. and Handley, M. K. (1987) Figwort mosaic virus: properties of the virus and its adaption to a new host. Phytopathology 77: 1668–1673.

Shepherd, R. J. (1989) Biochemistry of DNA plant viruses. In: "The Biochemistry of Plants" (A. Marcus, ed.), pp 563–661, Academic Press, Inc., New York.

Takatsui, H., Yamauchi, H., Watanabe, S., Kato, H., and Ikeda, J-E. (1992) Cauliflower mosaic virus reverse transcriptase: Activation by proteolytic processing and functional alteration by terminal deletion. J. Biol. Chem. 267: 11579–11585.

Thomas, C. L., Perbal, C., and Maule, A. J. (1993) A mutation in cauliflower mosaic virus gene I interferes with virus movement but not virus replication. Virology 192: 415–421.

Thomson, D., and Henry, R. (1993) Use of DNA from dry leaves for PCR and RAPD analysis. Plant Mol. Biol. Rep. 11: 202–206.

Wagner, G. J. 1992. Improving tobacco through metabolic engineering: Promise and obstacles. Rec, Adv. Tobacco. Sci. 18: 3–43.

Woolston, C. J., Covey, S. N., Penswick, J. R. and Davies, J. W. (1983) Aphid transmission and polypeptide are specified by a defined region of the cauliflower virus genome. Gene 23: 15–21.

Wurch, T., Guidasci, T, Geildreich, A., Lebeurier, G., and Mesnard, J-M. (1991) The cauliflower mosaic virus ORF VII product can be expressed in yeast but is not detected in infected plants. J. Virol. 64: 2594–2598.

Yanagisawa, S. and Izui, K. 1992. MNF1, a leaf tissue-specific DNA-binding protein of maize, interacts with the cauliflower mosaic virus 35S promoter as well as the C4 photosynthetic phosphoenolpyruvate carboxylase gene promoter. Plant mol. Biol. 19: 545–553.

Yeargan, R., Maiti, I. B., Nielsen, M. T., Hunt, A. G., and Wagner, G. J. 1992. Tissue partitioning of cadmium in transgenic tobacco seedlings and field grown plants expressing the mouse metallothionein I gene. Transgenic Research 1: 261–267.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. An isolated DNA molecule consisting essentially of restriction fragment Eco RI-Sma I of pUCFMV Flt103.

2. The isolated DNA molecule of claim 1 having the nucleotide sequence shown in SEQ ID NO: 2 from about residue 200 to about residue 405.

3. A plasmid comprising double enhancer regions from figwort mosaic virus, which enhancer regions have the nucleotide sequence shown in SEQ ID NO: 2 from about residue 200 to about residue 405.

4. The plasmid of claim 3, wherein the enhancer regions are contiguous.

5. A plasmid selected from the group consisting of pUCFMV Flt10, pUCFMV Ft101, pUCFMV Flt102, and pUCFMV Flt103.

6. An expression vector comprising a selectable marker gene, a promoter from figwort mosaic virus having a double enhancer region defined by Eco RI-Hind III restriction fragment from pUCFMV Flt10, and a multiple cloning site 3' to the promoter.

7. The expression vector of claim 6, wherein said enhancer region has the nucleotide sequence shown in SEQ ID NO: 2 from about residue 200 to about residue 405.

8. The expression vector of claim 6, further comprising a nucleotide sequence heterologous to the promoter, which is operably linked to said promoter.

9. The expression vector of claim 6, further comprising flanking left and right T-DNA border regions of *Agrobacterium tumefaciens*.

10. An expression vector selected from the group consisting of pKLF and pKLF2.

11. An expression vector comprising a selectable marker gene, a promoter region from figwort mosaic virus consisting essentially of the nucleotide sequence shown in SEQ ID NO: 2 from about residue 210 to about residue 522, and a multiple cloning site 3' to the promoter region.

12. The expression vector of claim 11, wherein the promoter region is that of pFMV CAT 20.

* * * * *